United States Patent
Cupps et al.

(10) Patent No.: US 6,486,190 B1
(45) Date of Patent: Nov. 26, 2002

(54) 5-(2-IMIDAZOLINYLAMINO)-BENZIMIDAZOLE DERIVATIVES, THEIR PREPARATION AND THEIR USE AS .ALPHA.-ADRENOCEPTOR AGONISTS WITH IMPROVED METABOLIC STABILITY

(75) Inventors: Thomas Lee Cupps, Norwich, NY (US); Sophie Eva Bogdan, Maineville, OH (US); Nick Nikolaides, Mason, OH (US); Sheri Ann Gilbert, Cincinnati, OH (US); Michael Gazda, Mason, OH (US); Roy Lee Dobson, Hamilton, OH (US); Charles Andrew III Cruze, West Chester, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/554,698

(22) PCT Filed: Nov. 20, 1998

(86) PCT No.: PCT/US98/24694

§ 371 (c)(1),
(2), (4) Date: May 18, 2000

(87) PCT Pub. No.: WO99/26942

PCT Pub. Date: Jun. 3, 1999

Related U.S. Application Data

(60) Provisional application No. 60/066,767, filed on Nov. 24, 1997, and provisional application No. 60/066,700, filed on Nov. 25, 1997.

(51) Int. Cl.[7] ................... A61K 31/4184; C07D 403/12
(52) U.S. Cl. ..................................... 514/394; 548/306.1
(58) Field of Search ........................ 548/306.1; 514/394

(56) References Cited

U.S. PATENT DOCUMENTS

| | | | |
|---|---|---|---|
| 3,890,319 A | 6/1975 | Danielewicz et al. | 260/250 |
| 4,029,792 A | 6/1977 | Danielewicz et al. | 424/251 |
| 4,036,976 A | 7/1977 | Neumann | 424/273 |
| 4,217,356 A | 8/1980 | Neumann | 424/270 |
| 4,398,028 A | 8/1983 | Neumann | 544/331 |
| 5,021,416 A | 6/1991 | Gluchowski | 514/249 |
| 5,091,528 A | 2/1992 | Gluchowski | 544/105 |
| 5,180,721 A | 1/1993 | Burke | 514/213 |
| 5,231,096 A | 7/1993 | Gluchowski et al. | 514/249 |
| 5,281,591 A | 1/1994 | Burke | 514/213 |
| 5,478,858 A | 12/1995 | Cupps et al. | 514/394 |
| 5,541,210 A | 7/1996 | Cupps et al. | 514/394 |
| 5,691,370 A | 11/1997 | Cupps et al. | 514/394 |

FOREIGN PATENT DOCUMENTS

| | | | |
|---|---|---|---|
| EP | 0025269 A1 | 3/1981 | A61K/31/155 |
| EP | 0047328 A1 | 3/1982 | C07D/403/12 |
| FR | 2638356 | 4/1990 | A61K/31/41 |
| WO | WO 92/21349 | 12/1992 | A61K/31/55 |
| WO | WO 95/16685 | 6/1995 | C07D/403/12 |
| WO | WO 96/04270 | 2/1996 | C07D/403/02 |

OTHER PUBLICATIONS

Cambridge, D., UK–14,304, A Potent and Selective $\alpha_2$–Agonist for the Characterization of $\alpha$–Adrenoceptor Subtypes:, *European Journal of Pharmacology*, vol. 72, pp. 413–415, (1981).

Chapleo, C.B., J.C. Doxey, P.L. Myers, M. Myers, C.F.C. Smith and M.R. Stillings, "Effect of 1,4–Dioxanyl Substitution on the Adrenergic Activity of Some Standard $\alpha$–Adrenoreceptor Agents", *European Journal of Medicinal Chemistry*, vol. 24, pp. 619–622, (1989).

Chapleo, C.B., R.C.M. Butler, D.C. England, P.L. Myers, A.G. Roach, C.F.C. Smith, M.R. Stillings and I.F. Tulloch, "Heteroaromatic Analogues of the $\alpha_2$–Adrenoreceptor Partial Agonist Clonidine", *J. Med. Chem.*, vol. 32, pp. 1627–1630, (1989).

Clare, K.A., M.C. Scrutton and N.T. Thompson, "Effects of $\alpha_2$–Adrenoreceptor Agonists and of Related Compounds on Aggregation of, and on Adenylate Cyclase Activity in, Human Platelets", *Br. J. Pharmac*, vol. 82, pp. 467–476, (1984).

Megens, A.A.H.P., J.E. Leysen, F.H.L. Awouters and C.J.E. Niemegeers, "Further Validation of In Vivo and In Vitro Pharmacological Procedures for Assessing the $\alpha_2/\alpha_1$–Selectivity of Test Compounds: (2) $\alpha$–Adrenoceptor Agonists", *European Journal of Pharmacology*, vol. 129, pp. 57–64, (1986).

Timmermans, P.B.M.W.M. and P.A. van Zwieten, "$\alpha_2$–Adrenoreceptor Agonists and Antagonists", *Drugs of the Future*, vol. 9, No. 1, pp. 41–55, (1984).

Timmermans, P.B.M.W.M., A.T. Chiu and M.J.M.C. Thoolen, "12.1 $\alpha$–Adrenergic Receptors", *Comprehensive Medicinal Chemistry*, vol. 3, Membranes & Receptors, pp. 133–185, (1990).

(List continued on next page.)

Primary Examiner—Laura L. Stockton
(74) Attorney, Agent, or Firm—David V. Upite; James C. Kellerman

(57) ABSTRACT

Benzimidazole compounds having the generic structure:

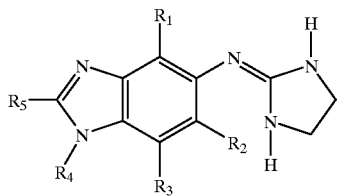

are used to treat alpha-2 mediated disorders, including nasal congestion, glaucoma, asthma, migraine, and diarrhea.

19 Claims, No Drawings

OTHER PUBLICATIONS

Timmermans P.B.M.W.M., A de Jonge, M.J.M.C. Thoolen, B. Wilffert, H. Batink, and P.A. van Zwieten, "Quantitative Relationships Between α–Adrenergic Activity and Binding Affinity of α–Adrenoceptor Agonists and Antagonists", *J. Med. Chem.*, vol. 27, No. 4, pp. 495–503, (1984).

van Meel, J.C.A., A. de Jonge, P.B.M.W.M. Timmermans and P.A. van Zwieten, "Selectivity of Some Alpha Adrenoceptor Agonists for Peripheral Alpha–1 and Alpha–2 Adrenoceptors in the Normotensive Rat", *The Journal of Pharmacology and Experimental Therapeutics*, vol. 219, No. 3, pp. 760–767, (1981).

Zilnchenko, "Study of the Autoallergenic Effect of Dibutyl and Dioctyl Phthalates", *All Union Scientific Research Institute of the Hygiene and Toxicology of Pesticides, Polymers, and Plastics*, Kiev, 1985. (Includes original Russian article and translation).

5-(2-IMIDAZOLINYLAMINO)-BENZIMIDAZOLE DERIVATIVES, THEIR PREPARATION AND THEIR USE AS .ALPHA.-ADRENOCEPTOR AGONISTS WITH IMPROVED METABOLIC STABILITY

This application is a 371 of PCT/US98/24694 filed Nov. 20, 1998 which claims the benefit of U.S. Provisional Applications 60/066,767 filed Nov. 24, 1997 and 60/066,780 filed Nov. 25, 1997.

TECHNICAL FIELD

The subject invention is directed to certain substituted benzimidazole compounds that have improved resistance to metabolism in primates. The subject compounds are alpha adrenoceptor agonists and are useful in treating alpha agonist associated disorders.

BACKGROUND OF THE INVENTION

Alpha adrenergic receptors, agonists, antagonists, and compounds related in structure to those of this invention are disclosed in the following references: Timmermans, P. B. M. W. M., A. T. Chiu & M. J. M. C. Thoolen, "12.1α-Adrenergic Receptors", *Comprehensive Medicinal Chemistry*, Vol. 3, Membranes & Receptors, P. G. Sammes & J. B. Taylor, eds., Pergamon Press (1990), pp. 133–185; Timmermans, P. B. M. W. M. & P. A. van Zwieten, "α-Adrenoceptor Agonists and Antagonists", *Drugs of the Future*, Vol. 9, No. 1, (January, 1984), pp. 41–55; Megens, A. A. H. P., J. E. Leysen, F. H. L. Awouters & C. J. E. Niemegeers, "Further Validation of in vivo and in vitro Pharmacological Procedures for Assessing the $\alpha_1$ and $\alpha_2$-Selectivity of Test Compounds: (2) α-Adrenoceptor Agonists", *European Journal of Pharmacology*, Vol. 129 (1986), pp. 57–64; Timmermans, P. B. M. W. M., A. de Jonge, M. J. M. C. Thoolen, B. Wilffert, H. Batink & P. A. van Zwieten, "Quantitative Relationships between α-Adrenergic Activity and Binding Affinity of α-Adrenoceptor Agonists and Antagonists", *Journal of Medicinal Chemistry*, Vol. 27 (1984) pp. 495–503; van Meel, J. C. A., A. de Jonge, P. B. M. W. M. Timmermans & P. A. van Zwieten, "Selectivity of Some Alpha Adrenoceptor Agonists for Peripheral Alpha-1 and Alpha-2 Adrenoceptors in the Normotensive Rat", *The Journal of Pharmacology and Experimental Therapeutics*, Vol. 219, No. 3 (1981), pp. 760–767; Chapleo, C. B., J. C. Doxey, P. L. Myers, M. Myers, C. F. C. Smith & M. R. Stillings, "Effect of 1,4-Dioxanyl Substitution on the Adrenergic Activity of Some Standard α-Adrenoreceptor Agents", *European Journal of Medicinal Chemistry*, Vol. 24 (1989), pp. 619–622; Chapleo, C. B., R. C. M. Butler, D. C. England, P. L. Myers, A. G. Roach, C. F. C. Smith, M. R. Stillings & I. F. Tulloch, "Heteroaromatic Analogues of the $\alpha_2$-Adrenoreceptor Partial Agonist Clonidine", *J. Med. Chem.*, Vol. 32 (1989), pp. 1627–1630; Clare, K. A., M. C. Scrutton & N. T. Thompson, "Effects of $\alpha_2$-Adrenoceptor Agonists and of Related Compounds on Aggregation of, and on Adenylate Cyclase Activity in, Human Platelets", *Br. J. Pharmac.*, Vol. 82 (1984), pp. 467–476; U.S. Pat. No. 3,890,319 issued to Danielewicz, Snarey & Thomas on Jun. 17, 1975; and U.S. Pat. No. 5,091,528 issued to Gluchowski on Feb. 25, 1992.

Alpha-2 adrenergic agonists are useful for treating a variety of disorders including: respiratory disorders (e.g., asthma, nasal congestion, COPD, cough, cystic fibrosis), gastrointestinal disorders (e.g., diahrrea, irritable bowel syndrome), ocular disorders (e.g., glaucoma), cardiovascular disorders (e.g., myocardial ischemia, shock, arrhythmias, angina, congestive heart failure), benign prostatic hypertrophy and migraine. However, many compounds disclosed in the art and related in structure to those of this invention are not alpha-2 adrenoceptor selective (e.g., they interact with other alpha receptors such as alpha-1 adrenoceptors). Alpha-2 adrenoceptor selectivity is desirable when treating alpha-2 associated or alpha-2 mediated disorders. For example, alpha-2 adrenergic agonists that possess significant alpha-1 adrenergic effects are known to cause cardiovascular side effects such as hypertension. In addition, many compounds disclosed in the art and related in structure to those of this invention possess significant central nervous system (CNS) activity which may lead to undesirable side effects such as severe sedation.

It has also been observed that some alpha adrenergic agonists are subject to extensive metabolic transformation in primates. Such metabolic transformation results in inactivation of the parent compound or in the formation of an active metabolite with a different pharmacological profile from the parent compound. Of particular importance to the present invention is the metabolic transformation that occurs to some alpha adrenergic benzimidazoles that are peripherally acting alpha-2-adrenoceptor selective agonists. Metabolic N-methylation at the benzimidazole ring may result in compounds that (1) are inactive; (2) are alpha-2 adrenoceptor antagonists; (3) possess enhanced activity at other undesired receptors, such as at alpha-1 adrenoceptors; and/or (4) have an increased potential for CNS activity. Thus, there is a continuing need for peripherally acting selective alpha-2 adrenergic compounds that have lower CNS activity and that resist metabolic transformation into undesirable compounds.

SUMMARY OF THE INVENTION

The present invention is directed to compounds having a structure according to the following formula:

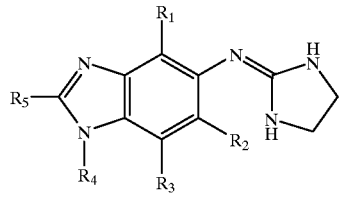

wherein:
(a) R1 is alkyl;
(b) R2 is selected from the group consisting of: hydrogen, alkyl, methoxy, cyano, and halo;
(c) R3 is selected from the group consisting of: hydrogen, methyl, hydroxy, cyano and halo;
(d) R4 is selected from the group consisting of: hydrogen, methyl, ethyl and isopropyl;
(e) R5 is selected from the group consisting of: hydrogen, methyl, amino, methoxy, hydroxy, cyano and halo;
(f) provided that at least one of R2, R3, R4 or R5 is other than hydrogen or fluorine;
(g) provided that when R1 is methyl and both R2 and R5 are hydrogen, R3 is other than methyl or halo;
(h) provided that when R3 is cyano, R1 is methyl; and
any tautomer of the above structure or a pharmaceutically acceptable salt, or biohydrolyzable ester, amide, or imide thereof.

The compounds of the present invention are useful in treating many medical disorders, including for example, respiratory disorders, ocular disorders, gastrointestinal disorders, disorders associated with sympathetic nervous system activity, migraine, peripheral pain, and disorders where vasoconstriction would provide a benefit. Accordingly, the invention further provides pharmaceutical compositions comprising these compounds. The invention still further provides methods of treatment using these compounds or the compositions containing them.

DETAILED DESCRIPTION OF THE INVENTION

Terms and Definitions

"Alkyl" is an unsubstituted saturated or unsaturated hydrocarbon chain having 1 to 3 carbon atoms. Alkyl chains may be straight, branched or cyclized. Preferred alkyl groups are methyl, ethyl, and cyclopropyl.

"Biohydrolyzable amide" refers to an amide of a compound of the invention that is readily converted in vivo by a subject to yield an active compound of the invention.

"Biohydrolyzable ester" refers to an ester of a compound of the invention that is readily converted by a subject to yield an active compound of the invention.

"Halo", "halogen", or "halide" is a chloro, bromo, fluoro or iodo. Preferred halo are chloro, bromo, and iodo. More preferred halo are chloro and bromo.

"Pharmaceutically-acceptable salt" is a cationic salt formed at any acidic (e.g., carboxyl) group, or an anionic salt formed at any basic (e.g., amino) group. Many such salts are known in the art, as described in World Patent Publication 87/05297, Johnston et al., published Sep. 11, 1987, incorporated by reference herein. Preferred cationic salts include the alkali metal salts (such as sodium and potassium), alkaline earth metal salts (such as magnesium and calcium) and organic salts. Preferred anionic salts include halides, sulfonates, carboxylates, phosphates, and the like. Clearly contemplated in such salts are addition salts that may provide an optical center, where once there was none. For example, a chiral tartrate salt may be prepared from the compounds of the invention, and this definition includes such chiral salts.

"Primate" includes humans.

Compounds

The present invention involves compounds having the following structure:

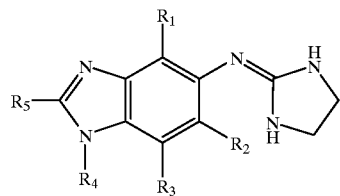

In the above structure, R1 is alkyl. Preferred R1 is methyl, ethyl or cyclopropyl.

In the above structure, R2 is hydrogen, alkyl, methoxy, cyano, or halo. Preferred R2 is hydrogen, alkyl, or cyano. More preferred R2 is methyl or halo.

In the above structure, R3 is hydrogen, methyl, hydroxy, cyano or halo. Preferred R3 is cyano or hydroxy when R1 is methyl. Most preferred R3 is cyano when R1 is methyl. Preferred R3 is methyl or halo when R1 is other than methyl.

In the above structure, R4 is hydrogen, methyl, ethyl or isopropyl. Preferred R4 is hydrogen or methyl, more preferably hydrogen.

In the above structure, R5 is hydrogen, methyl, amino, methoxy, hydroxy, cyano or halo. Preferred R5 is hydrogen, methyl, or halo.

In the above structure, at least one of R2, R3, R4, and R5 is other than hydrogen or fluorine. In addition, when R1 is methyl and both R2 and R5 are hydrogen, then R3 is other than methyl or halo. Finally, when R3 is cyano, R1 is methyl.

The invention includes tautomers of the above structure. For example, when tautomer D of a molecule is shown (see below), it is understood to include tautomer E. Thus, the disclosure of one tautomeric form discloses each and all of the tautomers.

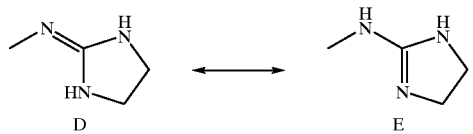

The invention also includes pharmaceutically acceptable acid addition salts, biohydrolyzable esters, amides, and imides of the above structure.

The compounds of the invention are sufficiently basic to form acid-addition salts. The compounds are useful both in the free base form and the form of acid-addition salts, and both forms are within the purview of the invention. The acid-addition salts are in some cases a more convenient form for use. In practice, the use of the salt form inherently amounts to the use of the base form of the active. Acids used to prepare acid-addition salts include preferably those which produce, when combined with the free base, medicinally acceptable salts. These salts have anions that are relatively innocuous to the animal organism, such as a mammal, in medicinal doses of the salts so that the beneficial property inherent in the free base are not vitiated by any side effects ascribable to the acid's anions.

Examples of appropriate acid-addition salts include, but at not limited to hydrochloride, hydrobromide, hydroiodide, sulfate, hydrogensulfate, acetate, trifluoroacetate, nitrate, maleate, citrate, fumarate, formate, stearate, succinate, mallate, malonate, adipate, glutarate, lactate, propionate, butyrate, tartrate, methanesulfonate, trifluoromethanesulfonate, p-toluenesulfonate, dodecyl sulfate, cyclohexanesulfamate, and the like. However, other appropriate medicinally acceptable salts within the scope of the invention are those derived from other mineral acids and organic acids. The acid-addition salts of the basic compounds are prepared by several methods. For example the free base can be dissolved in an aqueous alcohol solution containing the appropriate acid and the salt is isolated by evaporation of the solution. Alternatively, they may be prepared by reacting the free base with an acid in an organic solvent so that the salt separates directly. Where separation of the salt is difficult, it can be precipitated with a second organic solvent, or can be obtained by concentration of the solution.

Although medicinally acceptable salts of the basic compounds are preferred, all acid-addition salts are within the scope of the present invention. All acid-addition salts are useful as sources of the free base form, even if the particular salt per se is desired only as an intermediate product. For example, when the salt is formed only for purposes of purification or identification, or when it is used as an intermediate in preparing a medicinally acceptable salt by ion exchange procedures, these salts are clearly contemplated to be a part of this invention.

The compounds of the invention are useful for the treatment of a variety of diseases, disorders, and conditions that are modulated by alpha-2 adrenoceptors or by alpha-2 adrenoceptor activity. As used herein, the terms "disease," "disorder" and "condition" are used interchangeably. As used herein, a disorder described by the terms "modulated by alpha-2 adrenoceptors," or "modulated by alpha-2 adrenoceptor activity" refers to a disorder, condition or disease where alpha-2 adrenoceptor activity is an effective means of alleviating the disorder or one or more of the biological manifestations of the disease or disorder; or interferes with one or more points in the biological cascade either leading to the disorder or responsible for the underlying disorder; or alleviates one or more symptoms of the disorder. Thus, disorders subject to "modulation" include those for which:

The lack of alpha-2 activity is a "cause" of the disorder or one or more of the biological manifestations, whether the activity was altered genetically, by infection, by irritation, by internal stimulus or by some other cause;

The disease or disorder or the observable manifestation or manifestations of the disease or disorder are alleviated by alpha-2 activity. The lack of alpha-2 activity need not be causally related to the disease or disorder or the observable manifestations thereof;

Alpha-2 activity interferes with part of the biochemical or cellular cascade that results in or relates to the disease or disorder. In this respect, the alpha-2 activity alters the cascade, and thus controls the disease, condition or disorder.

The compounds of the invention are peripherally-selective alpha-2 adrenoceptor agonists. Alpha-2 adrenoceptors are distributed both inside and outside of the central nervous system. Thus, for example, a compound which displays a higher degree of central nervous system activity is preferred, but not limited to, use in central nervous system indications such as certain cardiovascular disorders (e.g., hypertension), pain, substance abuse and/or withdrawal. By centrally acting it is meant that they have some action on the alpha-2 adrenoceptors in the central nervous system in addition to their action at peripheral alpha-2 adrenoceptors.

Peripherally-acting compounds are preferred for, but not limited to, the treatment of respiratory disorders, ocular disorders, migraine, certain cardiovascular disorders, and certain gastrointestinal disorders. By peripherally acting, it is meant is that these compounds do not readily cross the blood-brain barrier and thus act primarily on alpha-2 adrenoceptors in the periphery. In addition, further specificity of action of these compounds can be achieved by delivering the agent to the region where activity is desired (for example, topical administration to the eye, nasal mucosa or respiratory tract), thereby reducing systemic exposure. Such peripherally-selective compounds have reduced CNS side effect potentials, particularly with respect to sedation. Methods are available in the art to determine which compounds are less centrally-acting than others.

The compounds of the subject invention have no or only weak alpha-1 agonist activity and have little or no effect on the central nervous system, even when dosed systemically.

Thus, the compounds of the invention are particularly useful for the treatment of respiratory disorders including nasal congestion associated with allergies, colds, and other nasal disorders, (as well as the sequelae of congestion of the mucous membranes, for example, sinusitis and otitis media), cough, chronic obstructive pulmonary disease and asthma. At effective doses, it has been found that undesired side effects can be avoided.

The compounds of the invention are also useful for the treatment of ocular disorders such as ocular hypertension, glaucoma, hyperemia, conjunctivitis, and uveitis.

The compounds of the invention are also useful for controlling gastrointestinal disorders, such as diarrhea, irritable bowel syndrome, hyperchlorhydria and peptic ulcer.

The compounds of the invention are also useful for diseases and disorders associated with sympathetic nervous system activity, including hypertension, myocardial ischemia, cardiac reperfusion injury, angina, cardiac arrhythmia, heart failure and benign prostatic hypertrophy.

The compounds of the invention are also useful for the prophylactic or acute treatment of migraine.

The compounds of the invention are also useful for the treatment of peripheral pain states associated with various disorders (for example, peripheral neuralgia).

The compounds of the invention are also useful for other diseases and disorders where vasoconstriction, particularly of veins, would provide a benefit, including septic or cardiogenic shock, elevated intracranial pressure, hemmorhoids, venous insufficiency, varicose veins, and menopausal flushing.

The pharmacological activity and selectivity of these compounds can be determined using published test procedures. The alpha-2 selectivity of the compounds is determined by measuring receptor binding affinities and in vitro functional potencies in a variety of tissues known to possess alpha-2 and/or alpha-1 receptors. (See, e.g., *The Alpha-2 Adrenergic Receptors,* L. E. Limbird, ed., Humana Press, Clifton, N.J.) The following in vivo assays are typically conducted in rodents or other species. Central nervous system activity is determined by measuring locomotor activity as an index of sedation. (See, e.g., Spyraki, C. & H. Fibiger, "Clonidine-induced Sedation in Rats: Evidence for Mediation by Postsynaptic Alpha-2 Adrenoreceptors", *Journal of Neural Transmission,* Vol. 54 (1982), pp. 153–163). Nasal decongestant activity is measured using rhinomanometry as an estimate of nasal airway resistance. (See, e.g., Salem, S. & E. Clemente, "A New Experimental Method for Evaluating Drugs in the Nasal Cavity", *Archives of Otolaryngology,* Vol. 96 (1972), pp. 524–529). Antiglaucoma activity is determined by measuring intraocular pressure. (See, e.g., Potter, D., "Adrenergic Pharmacology of Aqueous Human Dynamics", *Pharmacological Reviews,* Vol. 13 (1981), pp. 133–153). Antidiarrheal activity is determined by measuring the ability of the compounds to inhibit prostaglandin-induced diarrhea. (See, e.g., Thollander, M., P. Hellstrom & T. Svensson, "Suppression of Castor Oil-Induced Diarrhea by Alpha-2 Adrenoceptor Agonists", *Alimentary Pharmacology and Therapeutics,* Vol. 5 (1991), pp. 255–262). Efficacy in treating irritable bowel syndrome is determined by measuring the ability of compounds to reduce the stress-induced increase in fecal output. (See, e.g., Barone, F., J. Deegan, W. Price, P. Fowler, J. Fondacaro & H. Ormsbee III, "Cold-restraint stress increases rat fecal pellet output and colonic transit", *American Journal of Physiology,* Vol. 258 (1990), pp. G329–G337). Antiulcer and reduction of hyperchlorhydria efficacy is determined by measuring the reduction in gastric acid secretion produced by these compounds (See, e.g., Tazi-Saad, K., J. Chariot, M. Del Tacca & C. Roze, "Effect of α2-adrenoceptor agonists on gastric pepsin and acid secretion in the rat", *British Journal of Pharmacology*, Vol. 106 (1992), pp. 790–796). Antiasthma activity is determined by measuring the effect of the compound on bronchoconstriction associated with pulmonary challenges such as inhaled antigens. (See, e.g., Chang, J. J. Musser & J. Hand, "Effects of a Novel Leukotriene $D_4$ Antagonist with 5-Lipoxygenase and Cyclooxygenase Inhibitory Activity, Wy-45,911, on Leukotriene-$D_4$- and Antigen-Induced Bronchoconstriction in Guinea Pig", *International Archives of Allergy and Applied Immunology*, Vol. 86 (1988), pp. 48–54; and Delehunt, J., A. Perruchound, L. Yerger, B. Marchette, J. Stevenson & W. Abraham, "The Role of Slow-Reacting Substance of Anaphylaxis in the Late Bronchial Response After Antigen Challenge in Allergic Sheep", *American Reviews of Respiratory Disease*, Vol. 130 (1984), pp. 748–754). Activity in cough is determined by measuring the number and latency of the cough response to respiratory challenges such as inhaled citric acid. (See, e.g., Callaway, J. & R. King, "Effects of Inhaled α2-Adrenoceptor and $GABA_B$ Receptor Agonists on Citric Acid-Induced Cough and Tidal Volume Changes in Guinea Pigs", *European Journal of Pharmacology*, Vol. 220 (1992), pp. 187–195). The sympatholytic activity of these compounds is determined by measuring the reduction of plasma catecholamines (See, e.g., R. Urban, B. Szabo & K. Starke "Involvement of peripheral presynaptic inhibition in the reduction of sympathetic tone by moxonidine, rilmenidine and UK 14,304", *European Journal of Pharmacology*, Vol. 282 (1995), pp. 29–37) or the reduction in renal sympathetic nerve activity (See, e.g., Feng, Q., S. Carlsson, P. Thoren & T. Hedner, "Effects of clonidine on renal sympathetic nerve -activity, natriuresis and diuresis in chronic congestive heart failure rats", *Journal of Pharmacology and Experimental Therapeutics*, Vol. 261 (1992), pp. 1129–1135), providing the basis for their benefit in heart failure and benign prostatic hypertrophy. The hypotensive effect of these compounds is measured directly as a reduction in mean blood pressure (See, e.g., Timmermans, P. & P. Van Zwieten, "Central and peripheral α-adrenergic effects of some imidazolidines", *European Journal of Pharmacology*, Vol. 45 (1977), pp. 229–236). Clinical studies have demonstrated the beneficial effect of alpha-2 agonists in the prevention of myocardial ischemia during surgery (See, e.g., Talke, P., J. Li, U. Jain, J. Leung, K. Drasner, M. Hollenberg & D. Mangano, "Effects of Perioperative Dexmedetomidine Infusion in Patients Undergoing Vascular Surgery", *Anesthesiology*, Vol. 82 (1995), pp. 620–633) and in the prevention of angina (See, e.g., Wright, R. A., P. Decroly, T. Kharkevitch & M. Oliver, "Exercise Tolerance in Angina is Improved by Mivazerol—an α2-Adrenoceptor Agonist", *Cardiovascular Drugs and Therapy*, Vol. 7 (1993), pp. 929–934). The efficacy of these compounds in cardiac reperfusion injury is demonstrated by measuring the reduction of cardiac necrosis and neutrophil infiltration (See, e.g., Weyrich, A., X. Ma, & A. Lefer, "The Role of L-Arginine in Ameliorating Reperfusion Injury After Myocardial Ischemia in the Cat", *Circulation*, Vol. 86 (1992), pp. 279–288). The cardiac antiarrhythmic effect of these compounds is demonstrated by measuring the inhibition of ouabain induced arrhythmias (See, e.g., Thomas, G. & P. Stephen, "Effects of Two Imidazolines (ST-91 and ST-93) on the Cardiac Arrhythmias and Lethality Induced by Ouabain in Guinea-Pig", *Asia-Pacific Journal of Pharmacology*, Vol. 8 (1993), pp.109–113; and Samson, R., J. Cai, E. Shibata, J. Martins & H. Lee, "Electrophysiological effects of α2-adrenergic stimulation in canine cardiac Purkinje fibers", *American Journal of Physiology*, Vol. 268 (1995), pp. H2024–H2035).

The vasoconstrictor activity of these compounds is demonstrated by measuring the contractile properties on isolated arteries and veins in vitro (See, e.g., Flavahan, N., T. Rimele, J. Cooke & M. Vanhoutte, "Characterization of Postjunctional Alpha-1 and Alpha-2 Adrenoceptors Activated by Exogenous or Nerve-Released Norepinephrine in the Canine Saphenous Vein", *Journal of Pharmacology and Experimental Therapeutics*, Vol. 230 (1984), pp. 699–705). The effectiveness of these compounds at reducing intracranial pressure is demonstrated by measurement of this property in a canine model of subarachnoid hemorrhage (See, e.g., McCormick, J., P. McCormick, J. Zabramski & R. Spetzier, "Intracranial pressure reduction by a central alpha-2 adrenoreceptor agonist after subarachnoid hemorrhage", *Neurosurgery*, Vol. 32 (1993), pp. 974–979). The inhibition of menopausal flushing is demonstrated by measuring the reduction of facial blood flow in the rat (See, e.g., Escott, K., D. Beattie, H. Connor & S. Brain, "The modulation of the increase in rat facial skin blood flow observed after trigeminal ganglion stimulation", *European Journal of Pharmacology*, Vol. 284 (1995), pp. 69–76) as demonstrated for alpha-2 adrenergic agonists on cutaneous blood flow in the tail (See, e.g., Redfern, W., M. MacLean, R. Clague & J. McGrath, "The role of alpha-2 adrenoceptors in the vasculature of the rat tail", *British Journal of Pharmacology*, Vol. 114 (1995), pp. 1724–1730). The antimigraine effect of these compounds is demonstrated by measuring the reduction of dural neurogenic inflammation to trigeminal ganglion stimulation in the rat (See, e.g., Matsubara, T., M. Moskowitz & Z. Huang, "UK-14,304, R(-)-alpha-methylhistamine and SMS 201–995 block plasma protein leakage within dura mater by prejunctional mechanisms", *European Journal of Pharmacology*, Vol. 224 (1992), pp. 145–150).

Metabolic Stability

It has been observed that some peripherally acting, alpha-2-selective adrenergic agonist benzimidazoles which appear metabolically stable in vitro and in vivo in rodents, are subject to metabolic transformation in primates (i.e., monkeys and humans) via N-methylation at the benzimidazole ring. Such metabolic transformation has been shown to alter the profile of these benzimidazoles such that they may be metabolized into compounds that (1) are inactive; (2) are alpha-2 adrenoceptor antagonists; (3) possess enhanced activity at other undesired receptors, such as at alpha-1 adrenoceptors; and/or (4) have an increased potential for CNS activity. The compounds of the present invention are peripherally acting selective alpha-2 adrenergic compounds that have lower CNS activity and that resist metabolic transformation into such undesirable compounds.

Metabolic stability of the compounds described above is evaluated in vitro in a precision cut liver slice assay and in vivo in pharmacokinetic studies in primates. The precision cut liver slice assay is a well recognized, validated in vitro model to study xenobiotic metabolism in animal species and humans. (See Ekins, S. "Past, present, and future applications of precision-cut liver slices for in vitro xenobiotic metabolism." (Department of Medicine and Therapeutics, University of Aberdeen, UK.) *Drug-Metab-Rev.* (November, 1996) Vol. 28, No. 4: pp. 591–623). This assay is used to evaluate the metabolic activity of alpha-2 adrenergic agonists. The assay provides data on the biotransformations taking place within intact hepatocytes of the species of interest. Thus the full compliment of phase I and phase II metabolic enzymes are available to metabolize the drug as is the case in vivo.

For the pharmacokinetic studies, the compounds are administered orally to cynomolgus monkeys and measurements of administered benzimidazole compounds and corresponding N-methyl metabolites are made using 100 μL aliquots of urine collected over various time-periods post-dose. Typically, a chemical homolog or stable-isotope-labeled internal standard is added to each sample and then diluted 100× in water. Ten μL of prepared sample is then analyzed by gradient HPLC, with tandem mass spectrometry detection. Single ion reaction monitoring schemes are employed to selectively detect the test compound, its N-methyl metabolite (if present), and the internal standard.

The compounds of the present invention show little to no metabolic N-methylation in these assays. In contrast, N-methyl metabolites were found for other alpha-2 selective benzimidazole compounds such as 5-(2-Imidazolinylamino)-4-methylbenzimidazole and 4-ethyl-5-(2-imidazolinylamino)benzimidazole. 5-(2-Imidazolinylamino)-4-methylbenzimidazole provides a very similar pharmacological profile to 7-cyano-5-(2-imidazolinylamino)-4-methylbenzimidazole (see Example 1 below). That is, both compounds are very potent and selective alpha-2 adrenergic agonists, with very low CNS activity. In the precision cut liver slice assay, there is no evidence of the methyl metabolite for 7-cyano-5-(2-imidazolinylamino)-4-methylbenzimidazole. However, 5-(2-imidazolinylamino)-4-methylbenzimidazole, is rapidly metabolized in this assay and it was found that its metabolite is an alpha-2 adrenergic agonist with a significantly higher potential for CNS activity than the parent compound. 4-ethyl-5-(2-imidazolinylamino)benzimidazole, another selective alpha-2 adrenergic agonist, is rapidly and extensively N-methylated in primates. Its metabolite is a very potent alpha-2 antagonist, rather than an alpha-2 agonist.

The results indicate that the metabolic transformation of benzimidazoles through N-methylation can lead to rapid formation of undesired metabolites that have different pharmacological effects relative to the parent compound and that these effects are not easily predictable. Without being bound by theory it is contemplated that the factor favorably affecting the metabolic stability of the benzimidazole compounds of this invention is the sterical hindrance provided by substituents in close proximity to the benzimidazole nitrogens.

The compounds of this invention can be made using conventional organic syntheses. Particularly preferred syntheses are carried out using the following general schemes, Schemes 1–5. In the following general reaction schemes, R1, R2, R3, R4, and R5 are as defined above. For clarity, R1, R2, R3, R4, and/or R5 do not appear on the intermediates within a specific scheme unless they are prepared or needed in that specific scheme. Preferably, $R_1$ is part of the starting material (see Scheme 1). R2 can be part of the starting material or introduced via amination or bromination followed by functional group manipulation (see Scheme 2). R3 can be part of the starting material (see Scheme 1) or obtained by manipulation of a carboxylic acid (see Scheme 3). R4 is introduced by alkylation of an aniline substrate prior to the benzimidazole ring formation (see Scheme 1). R5 or a direct precursor to R5 is introduced during the benzimidazole ring formation (see Scheme 4). Finally, the 5-(2-imidazolinylamino) group is conveniently obtained from the aminobenzimidazoles prepared according to Schemes 1–4 (see Scheme 5).

The starting materials depicted within the schemes are commercially available or are made from commercially available starting materials and methods known to one of ordinary skill in the art. The skilled artisan may change temperature, pressure, atmosphere, solvents, or the order of reactions as appropriate. Additionally, the skilled artisan may use protecting groups to block side reactions or increase yields as appropriate. All such modifications can be readily be carried out by the skilled artisan in the art of organic chemistry, and thus are within the scope of the invention.

Scheme 1

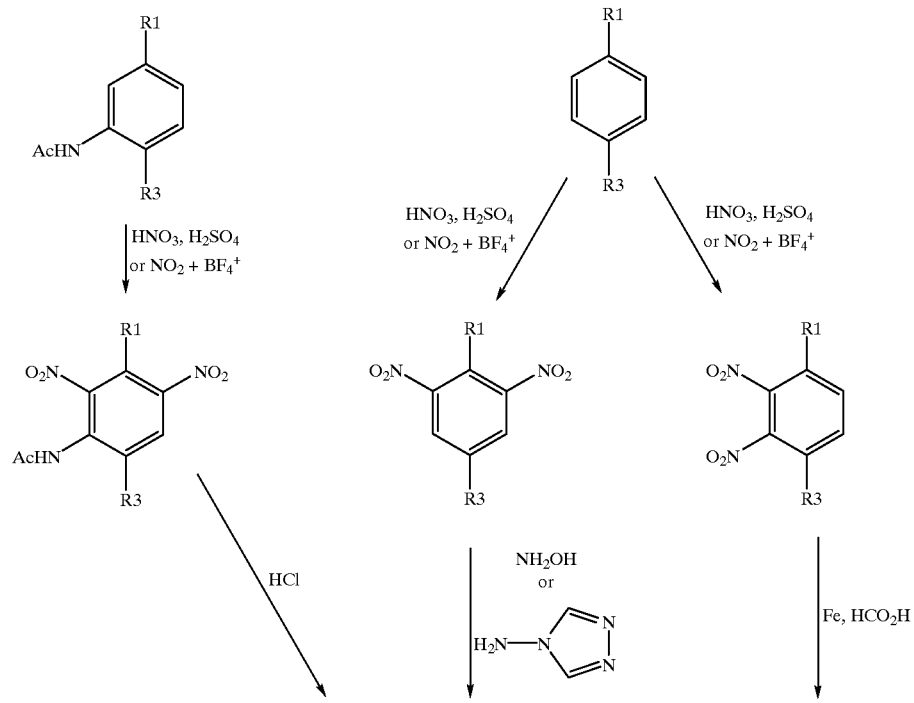

-continued
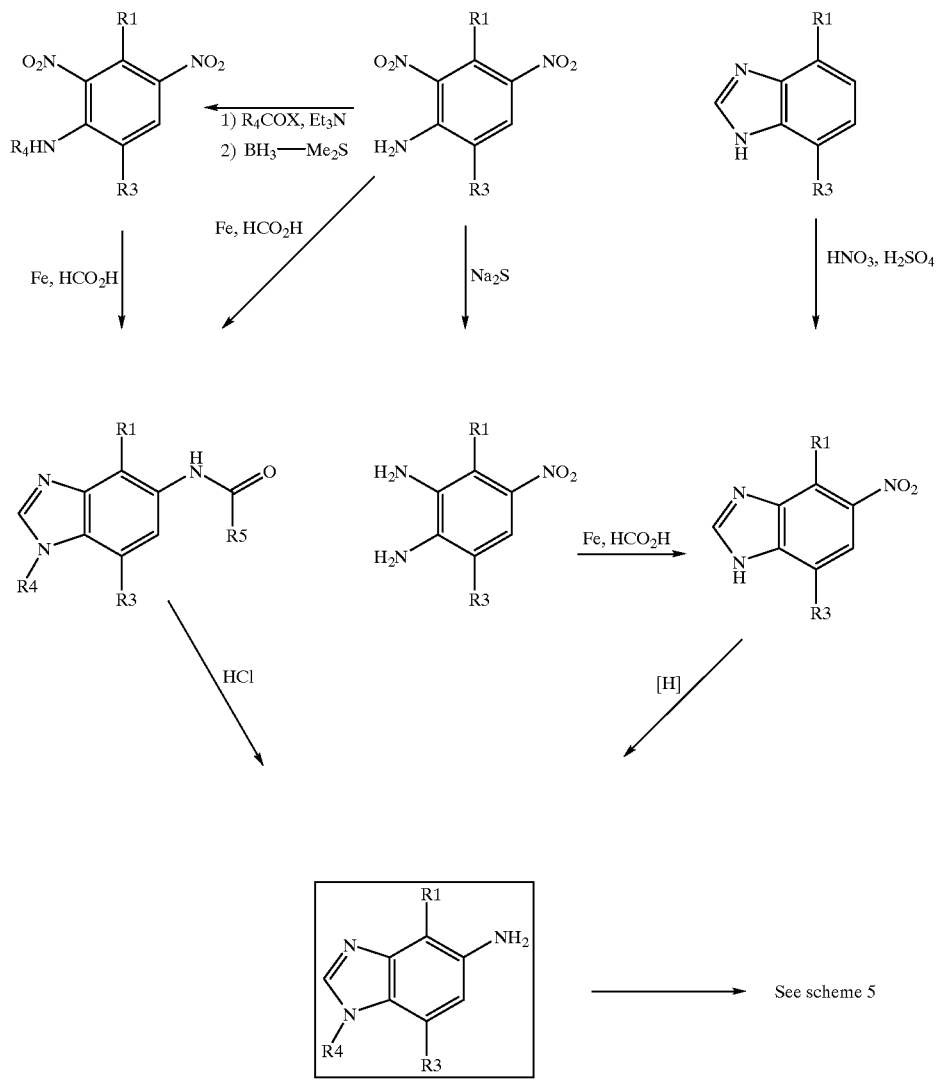
Scheme 2
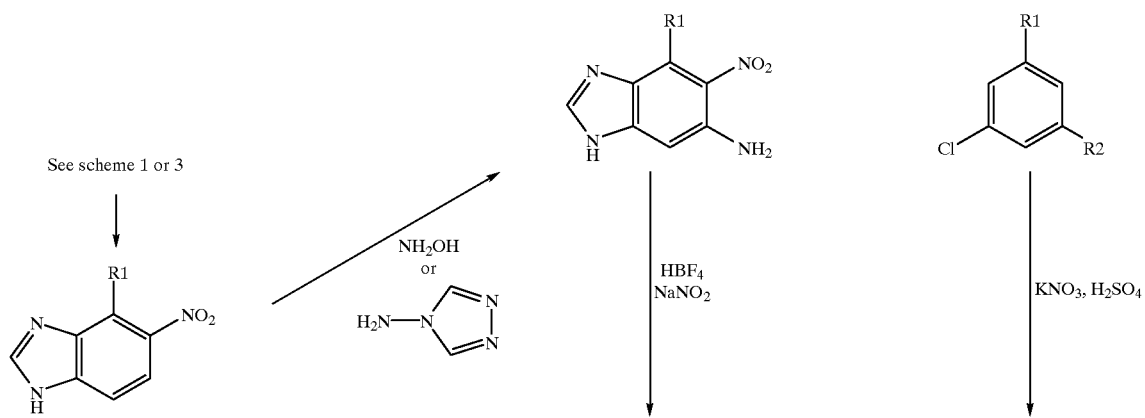

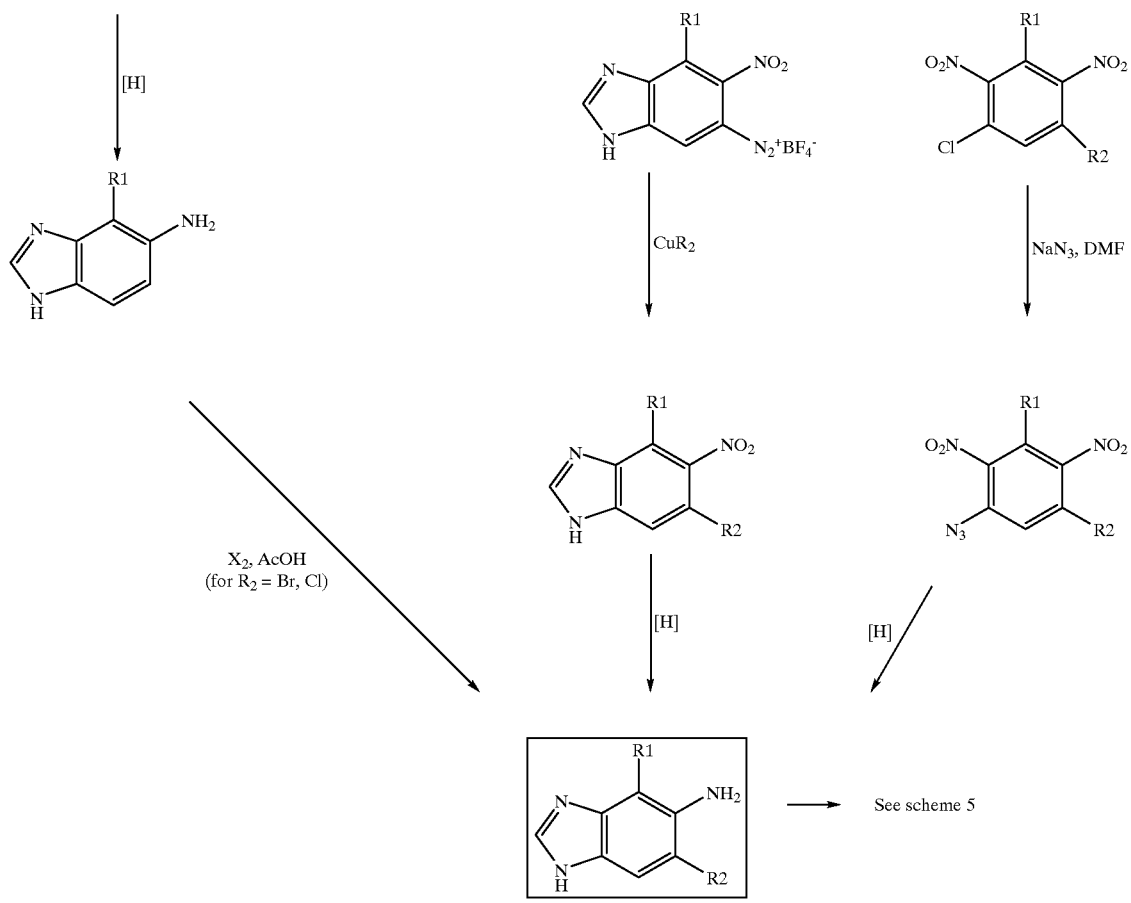
Scheme 3
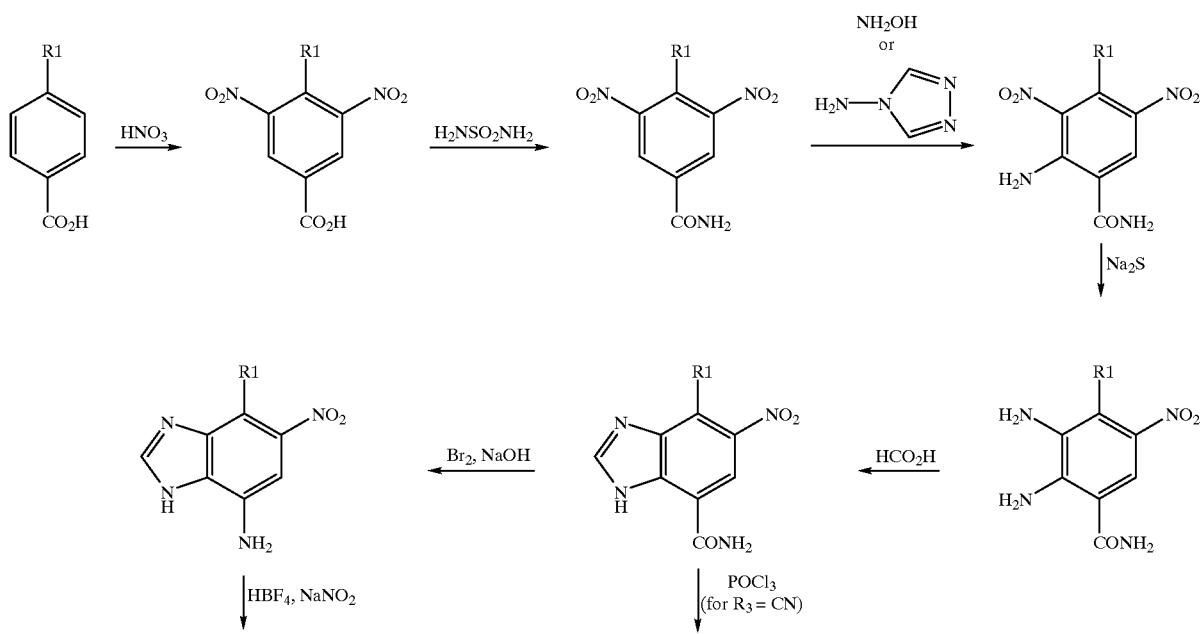

-continued
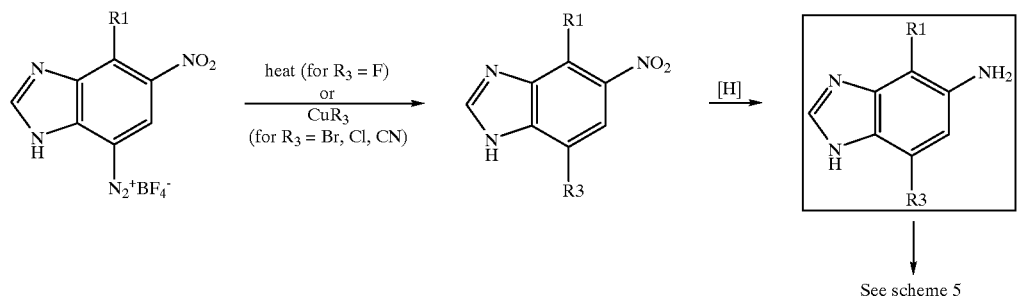
Scheme 4
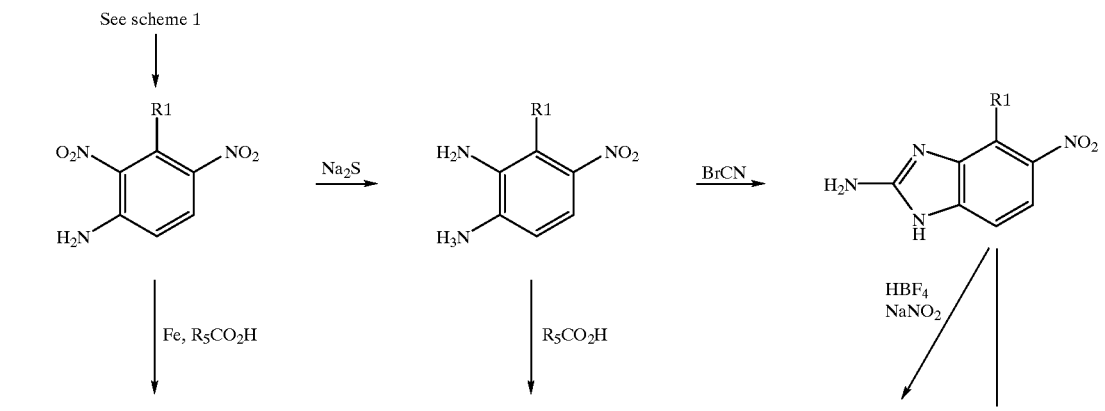
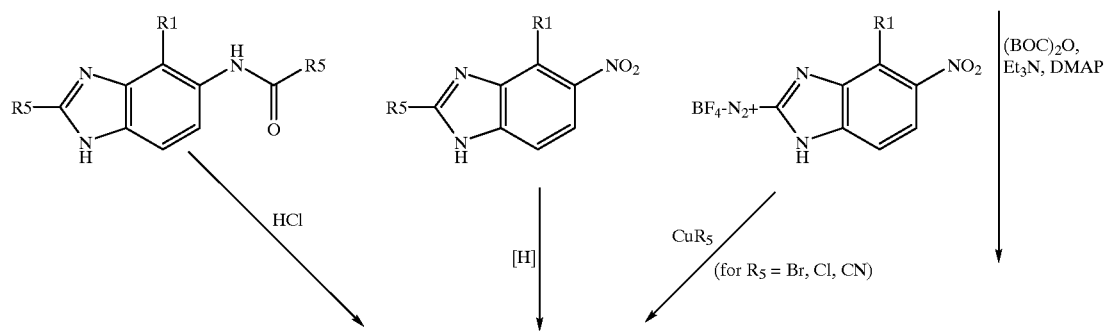
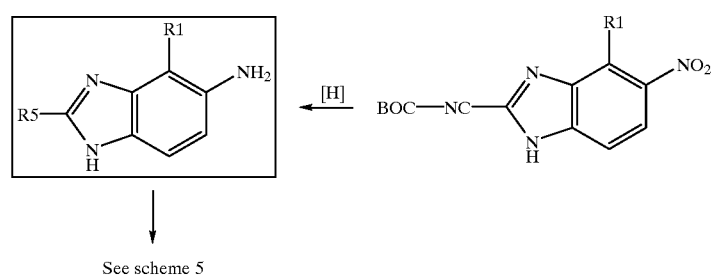

Scheme 5

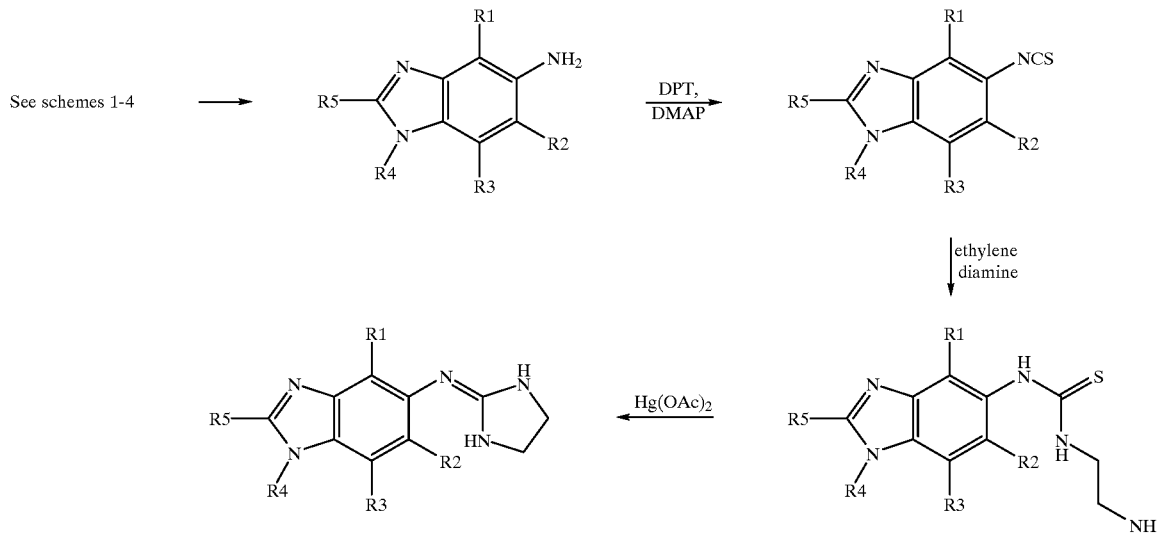

See schemes 1-4

EXAMPLES

The following non-limiting examples illustrate the compounds of the present invention.

Example 1

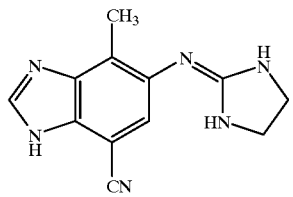

7-Cyano-5-(2-imidazolinylamino)-4-methylbenzimidazole 2,6-Dinitro-P-toluic acid. To a 500 mL roundbottom flask is added 120 mL of concentrated sulfuric acid. This is cooled to 0° C. and to this is added p-toluic acid (30 g, 0.22 mole). To this mixture is slowly added a mixture of fuming nitric acid (25 mL) and concentrated sulfuric acid (100 mL) via an addition funnel. The resulting mixture is then stirred at 0° C. for 10 minutes, slowly warmed first to room temperature, then to 90° C. for 1.5 hours. The mixture is cooled to room temperature and poured into ice/water. The resulting solid is then filtered and dried to afford 2,6-dinitro-p-toluic acid as an off-white solid.

2.6-Dinitro-p-toluic carboxamide. A mixture of 2,6-dinitro-p-toluic acid (15.14 g, 66.9 mmol) and sulfamide (14.79 g, 153.8 mmol) in anhydrous pyridine (80 mL) is stirred under an argon atmosphere at 100° C. for 3 hours. The mixture is poured into ice/water and the resulting precipitate is filtered and washed with water to afford 2,6-dinitro-p-toluic carboxamide as an off-white solid.

3-Amino-2,6-dinitro-p-toluic carboxamide. To a 1 L 3-neck round bottom flask equipped with a mechanical stirrer, are placed 2,6-dinitro-p-toluic carboxamide (4.0 g, 18 mmol) and hydroxylamine hydrochloride (3.3 g, 48 mmol) in ethanol (550 mL) and water (24 mL). The mixture is cooled to 0° C. and treated dropwise with a saturated solution of potassium hydroxide in methanol (80 mL) over a period of 1.5 hours. The resulting mixture is poured into a 2 L round bottom flask and diluted with 400 mL of water. The methanol and ethanol are then removed via rotary evaporation. A yellow precipitate formed which is filtered to give rise to 3-amino-2,6-dinitro-p-toluic carboxamide as fine yellow needles.

2,3-Diamino-6-nitro-p-toluic carboxamide. To a mixture of 3-amino-2,6-dinitro-p-toluic carboxamide (2.2 g, 9.2 mmol) in ethanol (200 mL) at 80° C. is added dropwise a solution of sodium sulfide (2.2 g, 28 mmol) in water (80 mL) over a period of one hour. The mixture is stirred at 80° C. for another 2 hours, then allowed to cool to room temperature and poured into ice. The mixture is extracted with ethyl acetate (5×300 mL). The combined extracts are dried over magnesium sulfate and rotary evaporated to give rise to 2,3-diamino-6-nitro-p-toluic carboxamide as a red/brown solid. The compound is used in the next step without further purification.

7-(4-Methyl-5-nitrobenzimidazolyl)carboxamide. A solution of 2,3-diamino-6-nitro-p-toluic carboxamide (1.49 g, 7.1 mmol) in formic acid (10 mL) is stirred at 100° C. for two hours. The solution is cooled to room temperature and poured into ice and basified to pH=10 with concentrated ammonium hydroxide. A brown precipitate forms which is filtered to afford 7-(4-methyl-5-nitrobenzimidazolyl) carboxamide as a tan solid.

7-Cyano-4-methyl-5-nitrobenzimidazole. A mixture of 7-(4-methyl-5-nitrobenzimidazolyl)carboxamide (1.5 g, 7.0 mmol) in phosphorous oxychloride (20 mL) and toluene (20 mL) is heated to reflux under an argon atmosphere for two hours. The mixture is cooled to room temperature, poured into ice and basified to pH=10 with concentrated ammonium hydroxide. The resulting mixture is extracted with 3:1 methylene chloride/isopropyl alcohol (6×100 mL), and the combined extracts dried over magnesium sulfate and rotary evaporated. The residue is purified by flash chromatography on silica gel, eluting with 9:1:0.1 chloroform:methanol:ammonium hydroxide to afford 7-cyano-4-methyl-5-nitrobenzimidazole as a yellow solid.

5-Amino-7-cyano-4-methylbenzimidazole. A mixture of 7-cyano-4-methyl-5-nitrobenzimidazole (0.91 g, 4.5 mmol) and 10% palladium-on-carbon (100 mg) in methanol (200 mL) is treated with an atmosphere of hydrogen (1 atm, balloon) for 14 hours. The resulting mixture is filtered through Celite and rotary evaporated. The residue is purified by flash chromatography (silica gel, 95:5 ethyl acetate:methanol) to afford 5-amino-7-cyano-4-methylbenzimidazole.

7-Cyano-5-isothiocyanato-4-methylbenzimidazole. To a solution of di-2-pyridylthionocarbonate (1.02 g, 3.1 mmol) and 4-dimethylaminopyridine (25 mg, 0.21 mmol) in tetrahydrofuran (350 mL) is added dropwise a solution of 5-amino-7-cyano-4-methylbenzimidazole (0.36 g, 2.1 mmol) in tetrahydrofuran (50 mL). The solution is stirred for one hour at room temperature. The reaction mixture is rotary evaporated and the residue is purified by flash chromatography (silica gel, 100% ethyl acetate) to give 7-cyano-5-isothiocyanato-4-methylbenzimidazole as an off-white solid.

N-5-(7-Cyano-4-methylbenzimidazolyl)-N'-2-aminoethylthiourea. A solution of 7-cyano-5-isothiocyanato-4-methylbenzimidazole (0.29 g, 1.35 mmol) in tetrahydrofuran (30 mL) is added dropwise to a solution of ethylenediamine (0.41 g, 6.8 mmol) in tetrahydrofuran (30 mL). A white precipitate forms after the solution has stirred at room temperature for 15 minutes. The reaction mixture is rotary evaporated to afford N-5-(7-cyano-4-methylbenzimidazolyl)-N'-2-aminoethylthiourea as an off-white solid.

7-Cyano-5-(2-imidazolinylamino)-4-methylbenzimidazole. To a 500 mL round bottom flask are added methanol (150 mL) and N-5-(7-cyano-4-methylbenzimidazolyl)-N'-2-aminoethylthiourea (0.31 g, 1.1 mmol). This mixture is heated slightly with a heat gun to provide a homogeneous mixture. To this mixture is added mercuric acetate (0.39 g, 1.2 mmol). The resulting mixture is stirred for 4 hours at room temperature then filtered through Celite and concentrated to afford 7-cyano-5-(2-imidazolinylamino)-4-methylbenzimidazole as a white foam.

Example 2

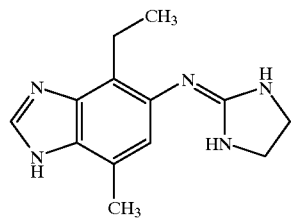

4-Ethyl-5-(2-imidazolinylamino)-7-methylbenzimidazole 3-(1-Hydroxyethyl)-6-methylaniline. To an ice-cold solution of 4-methyl-3-nitroacetophenone (25 g, 139 mmol) in methanol (200 mL) is added sodium borohydride (6.2 g, 163 mmol) over 15 minutes. The mixture is stirred at room temperature for 1 hour, then is quenched with water. The mixture is rotary evaporated and the residue is partitioned between water and ethyl acetate. The organic layer is dried (magnesium sulfate) and rotary evaporated to afford a light brown viscous oil. The oil is diluted with ethyl acetate (200 mL), 5% palladium-on-carbon (5 g) is added and the mixture is treated with hydrogen at 40 psi for 18 hours. The mixture is then filtered on Celite and the filtrate is rotary evaporated to afford 3-(1-hydroxyethyl)-6-methylaniline as a light yellow, pasty solid.

3-Ethyl-6-methylacetanilide. A mixture of 3-(1-hydroxyethyl)-6-methylaniline (21.3 g, 139 mmol), acetic anhydride (28 mL, 296 mmol), triethylamine (41 mL, 296 mmol) and 4-dimethylaminopyridine (0.5 g, 4 mmol) in methylene chloride (200 mL) is stirred at room temperature for 3 hours. Methanol (50 mL) is added and the mixture is rotary evaporated. The residue is partitioned between water and ethyl acetate. The organic layer is washed with water, 1N hydrochloric acid, water and brine, then dried (magnesium sulfate) and rotary evaporated. The residue is diluted with trifluoroacetic acid (100 mL) and cooled in an ice bath. Diethylsilane (35 mL, 270 mmol) is added and the resulting mixture is stirred at room temperature for 2 hours. The mixture is rotary evaporated and the residue is purified by flash chromatography on silica gel (hexane:ethyl acetate 3:1) to afford 3-ethyl-6-methylacetanilide as a foamy white solid.

2,4-Dinitro-3-ethyl-6-methylacetanilide. To an ice-cold mixture of 3-ethyl-6-methylacetanilide (11.5 g, 64.8 mmol) in conc. sulfuric acid (90 mL) is slowly added fuming nitric acid (7 mL). The mixture is stirred for 30 minutes in the ice bath, then for 1 hour at room temperature. The mixture is poured into ice and the solid that forms is collected by filtration, washed with water and dried under vacuum. The mixture of 2,4-dinitro-3-ethyl-6-methylacetanilide and 4,5-dinitro-3-ethyl-6-methylacetanilide is separated by flash chromatography on silica gel (hexane:ethyl acetate gradient 4:1 to 2:3).

2,4-Dinitro-3-ethyl-6-methylaniline. A mixture of 2,4-dinitro-3-ethyl-6-methylacetanilide (4.0 g, 14.9 mmol), potassium carbonate (2.6 g, 19 mmol) and 6N hydrochloric acid (40 mL) in methanol (100 mL) is heated to reflux for 2 hours. The mixture is cooled to room temperature, brought to pH 9 with ammonium hydroxide and rotary evaporated. The residue is purified by flash chromatography on silica gel (chloroform:methanol 9:1) to afford 2,4-dinitro-3-ethyl-6-methylaniline as a yellow solid.

4-Ethyl-5-formamido-7-methylbenzimidazole. A mixture of 2,4-dinitro-3-ethyl-6-methylaniline (2.0 g, 8.9 mmol) and iron powder (5.0 g, 90 mmol) in 90% formic acid (36 mL) is heated to reflux for 18 hours. The mixture is cooled to room temperature, diluted with methanol (75 mL) and filtered through Celite. The filtrate is rotary evaporated and the residue is purified by flash chromatography on silica gel (chloroform:methanol 9:1) to afford 4-ethyl-5-formamido-7-methylbenzimidazole as a tan solid.

5-Amino-4-ethyl-7-methylbenzimidazole. A mixture of 4-ethyl-5-formamido-7-methylbenzimidazole (1.7 g, 8.36 mmol), potassium carbonate (2.0 g, 14.4 mmol) and 6N hydrochloric acid (34 mL) in methanol (34 mL) is heated to reflux for 1 hour. The mixture is cooled to room temperature, brought to pH 9 with ammonium hydroxide and rotary evaporated. The residue is purified by flash chromatography on silica gel (chloroform:methanol 9:1) to afford 5-amino-4-ethyl-7-methylbenzimidazole as a tan solid.

4-Ethyl-5-isothiocyanato-7-methylbenzimidazole. To a mixture of di-2-pyridyl thionocarbonate (0.72 g, 3.11 mmol) and 4-dimethylaminopyridine (0.02 g) in ethyl acetate (50 mL) is added dropwise a solution of 5-amino-4-ethyl-7-methylbenzimidazole (0.42 g, 2.39 mmol) in ethyl acetate (20 mL) and methanol (5 mL). The mixture is stirred at room temperature for 3 hours, then rotary evaporated. The residue is purified by filtration on a short pad of silica gel, eluting with ethyl acetate, to afford 4-ethyl-5-isothiocyanato-7-methylbenzimidazole as a tan solid.

4-Ethyl-5-(2-imidazolinylamino)-7-methylbenzimidazole, trifluoroacetic acid salt. To a mixture of ethylenediamine (0.65 mL, 9.66 mmol) in methylene chloride (50 mL) is added a suspension of 4-ethyl-5-isothiocyanato-7-methylbenzimidazole (0.42 g, 1.93 mmol) in methylene chloride (50 mL). The mixture is stirred for 1 hour at room temperature, then rotary evaporated. The residue is diluted with methanol (100 mL) and mercuric acetate (0.74 g, 2.32 mmol) is added. The mixture is stirred at room temperature for 2 hours. The mixture is filtered on Celite with a methanol wash of the solids. The filtrate is rotary evaporated and the reside is purified by preparative High Pressure Liquid Chromatography (HPLC) (C18 column; flow rate 45 mL/min; solvent gradient: 0.1% trifluoroacetic acid (in water)/acetonitrile starting at 95/5 and going to 0/100 over 45 minutes) to afford 4-ethyl-5-(2-imidazolinylamino)-7-methylbenzimidazole as a trifluoroacetic acid salt.

Example 3

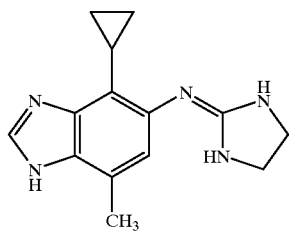

4-Cyclopropyl-5-(2-imidazolinylamino)-7-methylbenzimidazole

Commercially available 1-(4-methylphenyl)-1-cyclopropane carboxylic acid is treated with nitronium tetrafluoroborate in sulfolane to afford 1-(4-methyl-3-nitrophenyl)-1-cyclopropane carboxylic acid. This is converted to 1-(4-methyl-3-nitrophenyl)-1-bromocyclopropane by treatment with mercuric oxide and bromine in methylene chloride. Reduction with zinc dust in the presence of calcium chloride in aqueous ethanol affords 5-cyciopropyl-2-methylaniline. Conversion to 4-cyclopropyl-5-(2-imidazolinylamino)-7-methylbenzimidazole is completed in the same manner as 4-ethyl-5-(2-imidazolinylamino)-7-methylbenzimidazole (see Example 2).

Example 4

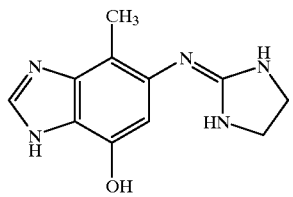

7-Hydroxy-5-(2-imidazolinylamino)-4-methylbenzimidazole (2-imidazolinylamino)-7-methoxy-4-methylbenzimidazole is made in the same manner as 4-ethyl-5-(2-imidazolinylamino)-7-methylbenzimidazole except that 2-methoxy-5-methylacetanilide is used instead of 3-ethyl-6-methylacetanilide (see Example 2). Cleavage of the methyl ether is achieved with pyridinium hydrochloride to afford 7-hydroxy-5-(2-imidazolinylamino)-4-methylbenzimidazole.

Example 5

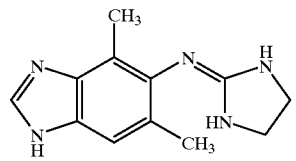

4,6-Dimethyl-5-(2-imidazolinylamino) benzimidazole

5-Chloro-2,4-dinitro-m-xylene. To ice cold concentrated sulfuric acid is added 5-chloro-m-xylene (10.0 g, 71 mmol). With vigorous stirring, solid potassium nitrate (14.35 g, 0.14 mol) is added slowly over 30 minutes. Upon completion of addition, the reaction mixture is warmed to room temperature and stirred for 2 hours. The solid that has formed is filtered and recrystallized from ethanol/water. This material is further purified by flash chromatography on silica gel (95:5 hexane:ethyl acetate) to afford 5-chloro-2,4-dinitro-m-xylene as a white crystalline solid.

5-Azido-2,4-dinitro-m-xylene. A mixture of 5-chloro-2, 4-dinitro-m-xylene (707 mg, 3.1 mmol), sodium azide (219 mg, 3.37 mmol) and N,N-dimethylformamide (10 mL) is heated at 80° C. for 45 minutes then cooled to room temperature, poured into ice/water and extracted with ethyl acetate (3×50 mL). The combined organic layers are dried (magnesium sulfate), filtered, and concentrated via rotary evaporation to provide 5-azido-2, 4-dinitro-m-xylene as a yellow/brown solid. (650 mg, 2.7 mmol), 10% palladium-on-carbon (100 mg) and 80% formic acid (20 mL) is heated to 80° C. for 30 minutes, cooled to room temperature, and filtered through a plug of silica gel (eluting with water). The filtrate is basified (~pH 10) with 28% ammonium hydroxide and extracted with ethyl acetate (3×100 mL). The combined organic layers are dried (magnesium sulfate), filtered, and concentrated to afford 4,6-dimethyl-5-nitrobenzimidazole as a yellow oil.

5-Amino-4,6-dimethylbenzimidazole. A heterogeneous mixture of 4,6-dimethyl-5-nitrobenzimidazole (410 mg, 2.14 mmol) and 10% palladium-on-carbon (50 mg) in methanol (25 mL) is treated with an atmosphere of hydrogen (1 atm, balloon) for 16 hours. The resulting mixture is filtered through Celite and rotary evaporated. The residue is purified by chromatography on silica gel (95:5 methylene chloride:methanol) to afford 5-amino-4,6-dimethylbenzimidazole as a white solid.

4,6-Dimethyl-5-isothiocyanatobenzimidazole. A mixture of 5-amino-4,6-dimethylbenzimidazole (265 mg, 1.64 mmol), tetrahydrofuran (20 mL), di-2-pyridylthionocarbonate (584 mg, 1.81 mmol), and 4-dimethylaminopyridine (20 mg, 0.016 mmol is stirred at room temperature for 2 hours. The mixture is rotary evaporated and the residue is purified by chromatography on silica gel (50:50 hexane:ethyl acetate) to provide 4,6-dimethyl-5-isothiocyanatobenzimidazole as an off-white solid.

4,6-Dimethyl-5-(2-imidazolinviamino)benzimidazole. A solution of 4,6-dimethyl-5-isothiocyanatobenzimidazole (250 mg, 1.23 mmol) in methylene chloride (5 mL) is added dropwise to a solution of ethylenediamine (370 mg, 6.2 mmol) in methylene chloride (5 mL). The resulting solution is stirred at room temperature for 15 minutes then rotary evaporated. The residue is dissolved in methanol (10 mL) and to this solution is added mercuric acetate (390 mg, 1.23 mmol). The resulting reaction mixture is stirred at room temperature for 1 hour, filtered through a pad of silica gel and rotary evaporated. The residue is purified by chromatography on silica gel (70:30:0.5 methylene chloride:methanol:ammonium hydroxide) to afford 4,6-dimethyl-5-(2-imidazolinylamino)benzimidazole as a white solid.

Example 6

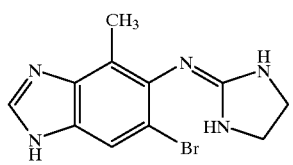

6-Bromo-5-(2-imidazolinylamino)-4-methylbenzimidazole

Commercially available 2,6-dinitrotoluene is converted to 5-amino-4-methylbenzimidazole according to scheme 1. Bromination is achieved by treatment with bromine in acetic acid. The synthesis is then completed according to Scheme 5.

Example 7

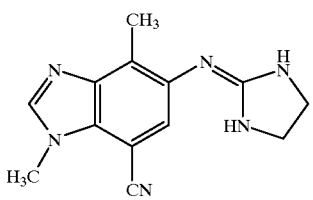

7-Cyano-1,4-dimethyl-5-(2-imidazolinylamino)benzimidazole

This compound is made according to a combination of Schemes 1 and 3 using 3-amino-2,6-dinitro-p-toluic carboxamide as prepared in Example 1.

Example 8

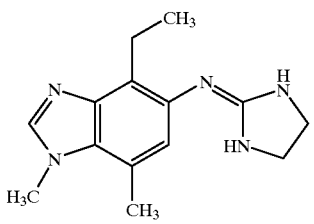

1,7-Dimethyl-4-ethyl-5-(2-imidazolinylamino)benzimidazole

This compound is made according to Scheme 1. 2,4-Dinitro-3-ethyl-6-methylaniline is treated with paraformaldehyde in concentrated sulfuric acid to afford N-methyl-2,4-dinitro-3-ethyl-6-methylaniline. The synthesis is completed in the same manner as 4-ethyl-5-(2-imidazolinylamino)benzimidazole (see Example 2).

Example 9

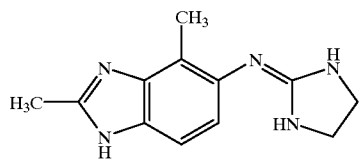

2,4-Dimethyl-5-(imidazolinylamino)benzimidazole 2,3-diamino-6-nitrotoluene. To a solution 3-methyl-2,4-dinitroaniline (30 g) in boiling ethanol (750 mL) is added dropwise over 90 minutes a solution of sodium sulfide nonahydrate (109.6 g) in water (750 mL). At the end of the addition, the mixture is heated to reflux for 30 minutes then poured into ice (2000 g) and allowed to stand until all the ice has melted. The mixture is then extracted with methylene chloride and the organic layer is dried over magnesium sulfate and rotary evaporated. The residue is purified by flash chromatography on silica get, eluting with methylene chloride to afford 2,3-diamino-6-nitrotoluene as an orange solid.

2,4-Dimethyl-5-nitrobenzimidazole. A mixture of 2,3-diamino-6-nitrotoluene (0.945 g, 5.65 mmol), conc. hydrochloric acid (5 mL) and glacial acetic acid (30 mL) is heated to reflux for 2 hours. The mixture is cooled to room temperature, then poured in a mixture of crushed ice (100 mL) and ammonium hydroxide (100 mL) and extracted with 20% methanol in chloroform (2×400 mL). The combined extracts are dried over potassium carbonate and rotary evaporated to afford 2,4-dimethyl-5-nitrobenzimidazole as a brown solid. The product is used in the following step without further purification.

1-t-Butoxycarbonyl-2,4-dimethyl-5-nitrobenzimidazole. A mixture of 2,4-methyl-5-nitrobenzimidazole (0.63 g, 4.3 mmol), di-t-butyl-dicarbonate (0.24 g, 10.8 mmol), triethylamine (0.725 mL, 5.2 mmol) and 4-dimethylaminopyridine (0.05 g) in ethyl acetate (45 mL) is stirred at room temperature overnight. The mixture is rotary evaporated and the residue purified by flash chromatography on silica gel, eluting with 10% ethyl acetate in hexane to afford 1-t-butoxycarbonyl-2,4-dimethyl-5-nitrobenzimidazole as a white solid.

5-Amino-1-t-butoxycarbonyl-2,4-dimethylbenzimidazole. To a solution of 1-t-butoxycarbonyl-2,4-dimethyl-5-nitrobenzimidazole (1.26 g, 4.32 mmol) in methanol (15 mL)/ethyl acetate (100 mL) are added 10% palladium-on-carbon (0.1 g) and ammonium formate (1.09 g, 17.3 mmol). The mixture is stirred at room temperature for 3 hours, then filtered on Celite with a methanol wash of the solids. The filtrate is rotary evaporated and the residue is purified by flash chromatography on silica gel, eluting with 20% ethyl acetate in hexane to afford 5-amino-1-t-butoxycarbonyl-2,4-dimethylbenzimidazole as a white solid.

1-t-Butoxycarbonyl-2,4-dimethyl-5-isothiocyanatobenzimidazole. A solution of 5-amino-1-t-butoxycarbonyl-2,4-dimethylbenzimidazole (1.1 g, 4.2 mmol) in methylene chloride (60 mL) is added dropwise over 30 minutes to a solution of di-2-pyridyl thionocarbonate (1.9 g, 8.2 mmol) and 4-dimethylaminopyridine (0.1 g) in methylene chloride (150 mL). The mixture is stirred for 2 hours at room temperature then rotary evaporated. The residue is purified by flash chromatography on silica gel, eluting with 10% ethyl acetate/hexane to afford 1-t-butoxycarbonyl-2,4-dimethyl-5-isothiocyanatobenzimidazole as a white solid.

N-(1-t-Butoxycarbonyl-2,4-dimethyl-5-benzimidazolyl)-N'-2-aminoethylthiourea. A solution of 1-t-butoxycarbonyl-2,4-dimethyl-5-isothiocyanatobenzimidazole (1.15 g, 3.8 mmol) in methylene chloride (100 mL) is added dropwise over 15 minutes to 1,2-ethylenediamine (1.26 mL, 18.9 mmol) in solution in methylene chloride (200 mL). The mixture is stirred for 2 hours at room temperature. The mixture is rotary evaporated and the residue is triturated with ether (150 mL) for 1 hour at room temperature. The solid is filtered and dried in vacuo to afford N-(1-t-butoxycarbonyl-2,4-dimethyl-5-benzimidazolyl)-N'-2-aminoethylthiourea as a white solid.

2,4-Dimethyl-5-(2-imidazolinviamino)benzimidazole. A mixture of N-(1-t-butoxycarbonyl-2,4-dimethyl-5-benzimidazolyl)-N'-2-aminoethylthiourea (1.33 g, 3.66 mmol) and mercuric acetate (1.45 g, 4.54 mmol) in methanol (150 mL) is stirred at room temperature for 1 hour. The resulting black mixture is filtered on Celite with a methanol wash of the solids. The filtrate is rotary evaporated and the residue is purified by flash chromatography on a short pad of silica gel, eluting with 10% methanol/chloroform containing 1% of ammonium hydroxide. The product-containing fractions are collected and rotary evaporated to afford 2,4-dimethyl-5-(2-imidazolinylamino)benzimidazole as a white solid.

Example 10

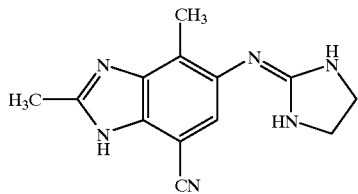

7-Cyano-2,4-dimethyl-5-(2-imidazolinylamino)benzimidazole

This compound is made according to Scheme 4 from 3-amino-2,6-dinitro-p-toluic carboxamide prepared in Example 1.

Example 11

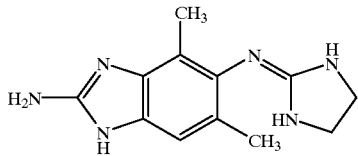

2-Amino-4,6-dimethyl-5-(2-imidazolinylamirio)benzimidazole

N-Acetyl-3,5-dimethylaniline. A mixture of 3,5dimethylaniline (20 g, 165 mmol), acetic anhydride (24 mL, 247 mmol) and triethylamine (70 mL, 495 mmol) in methylene chloride (300 mL is stirred at room temperature for 16 hours. The mixture is washed with water, dried (magnesium sulfate) and rotary evaporated. The residue is triturated with hexane and filtered to afford N-acetyl-3,5-dimethylaniline (25 g).

N-Acetyl-3,5-dimethyl-2,4-dinitroaniline. To a cold (ice) solution of N-acetyl-3,5-dimethylaniline (25 g, 153 mmol) in concentrated sulfuric acid (500 mL) is added potassium nitrate (48 g, 474 mmol). The mixture is stirred for 45 minutes at 0° C. then 15 hours at room temperature. The mixture is poured into ice/water and extracted with chloroform. The extract is dried (magnesium sulfate) and rotary evaporated. The residue is purified by flash chromatography on silica gel (30% ethyl acetate/hexane) to afford N-acetyl-3,5-dimethyl-2,4-dinitroaniline (14.6 g).

3,5-Dimethyl-2,4-dinitroaniline. A mixture of N-acetyl-3,5-dimethyl-2,4-dinitroaniline (14.6 g, 57 mmol) and sodium methoxide (25 wt % solution in methanol) (26 mL) and methanol (200 mL) is heated to reflux for 90 minutes. The mixture is rotary evaporated and the residue is partitioned between water and chloroform. The organic layer is dried (magnesium sulfate) and rotary evaporated. The residue is purified by flash chromatography on silica gel (25% ethyl acetateihexane) to afford 3,5-dimethyl-2,4-dinitroaniline (8.0 g) as an orange solid.

1,2-Diamino-3,5-dimethyl-4-nitrobenzene. A solution of 3,5-dimethyl-2,4-dinitroaniline (1.5 g, 7 mmol) in ethyl acetate (100 mL) is treated with hydrogen at atmospheric pressure for 2 hours. The mixture is filtered on Celite and the filtrate is rotary evaporated to afford 1,2-diamino-3,5-dimethyl4-nitrobenzene (1.25 g) as a red solid.

2-Amino-4,6-dimethyl-5-nitrobenzimidazole. A mixture of 1,2-diamino-3,5-dimethyl-4-nitrobenzene (0.87 g, 4.83 mmol) and cyanogen bromide (0.87 g, 7.73 mmol) in methanol (50 mL) is stirred at room temperature for 16 hours. The mixture is rotary evaporated to afford 2-amino-4,6-dimethyl-5-nitrobenzimidazole. The product is used in the next step without further purification.

2-(t-Butoxycarbonyl)amino-4,6-dimethyl-5-nitrobenzimidazole. A mixture of 2-amino-4,6-dimethyl-5-nitrobenzimidazole (1.3 g, 6.31 mmol), di-t-butyl dicarbonate (2.5 mL of 1M solution in tetrahydrofuran, 7.56 mmol), triethylamine (2.6 mL, 18.9 mmol) and dimethylaminopyridine (0.1 g) in 20% methanol/ethyl acetate (60 mL) is stirred at room temperature for 16 hours. The mixture is rotary evaporated. The residue is partitioned between chloroform and 3% aqueous sodium carbonate. The organic layer is dried (magnesium sulfate) and rotary evaporated. The residue is purified by flash chromatography on silica gel (30% ethyl acetate/hexane) to afford 2-(t-butoxycarbonyl)amino-4,6-dimethyl-5-nitrobenzimidazole.

5-Amino-2-(t-butoxycarbonyl)amino-4,6-dimethylbenzimidazole. A suspension of 2-(t-butoxycarbonyl)amino-4,6-dimethyl-5-nitrobenzimidazole (0.625 g, 2.04 mmol) in ethanol (70 mL) is treated with hydrogen at 45 psi for 15 hours. The mixture is filtered on Celite and the filtrate is rotary evaporated to afford 5-amino-2-(t-butoxycarbonyl)amino-4,6-dimethylbenzimidazole (0.5 g).

2-Amino-4,6-dimethyl-5-(2-imidazolinvlamino)benzimidazole. A mixture of 5-amino-2-(t-butoxycarbonyl)amino-4,6-dimethylbenzimidazole (0.4 g, 1.44 mmol), di-2-pyridyl thionocarbonate (1.0 g, 4.32 mmol) and dimethylaminopyridine (0.1 g) in methylene chloride (40 mL) and methanol (2 mL) is stirred at room temperature for 15 hours. This mixture is then slowly added to a solution of 1,2-ethylene diamine (0.6 mL, 8.97 mmol) in methylene chloride (10 mL). The resulting mixture is stirred at room temperature for 1 hour. The mixture is rotary evaporated and the residue is triturated with ethyl acetate and filtered. The solid is suspended in methanol (300 mL), mercuric acetate is added (0.56 g, 1.75 mmol) and the resulting mixture is stirred at room temperature for 15 hours. The mixture is filtered through Celite and the filtrate is rotary evaporated. The residue is purified by preparative HPLC (C4 column, solvent gradient: 0.1% trifluoroacetic acid (in water)/acetonitrile starting at 95/5 and going to 0/100) to afford 2-amino-4,6-dimethyl-5-(2-imidazolinylamino) benzimidazole as a trifluoroacetic acid salt.

Example 12

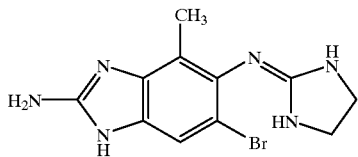

2-Amino-6-bromo-5-(2-imidazolinylamino)-4-methylbenzimidazole

This compound is prepared by a combination of Schemes 1 and 4. Commercially available 2,6-dinitrotoluene is converted to 2,3-diamino-6-nitrotoluene according to scheme 2. Reaction with cyanogen bromide affords 2-amino-4-methyl-5-nitrobenzimidazole. After protection of the amino group with a tert-butoxycarbonyl group, the compound is reduced by hydrogenation (palladium-on-carbon) and brominated (bromine, sodium acetate, acetic acid) to afford 5-amino-6-bromo-2-tert-butoxycarbonylamino-4-methylbenzimidazole. The formation of the 5-(2-imidazolinylamino) group is completed in the usual fashion and the tert-butoxycarbonyl group is cleaved by treatment with hydrobromic acid to afford 2-amino-6-bromo-5-(2-imidazolinylamino)-4-methylbenzimidazole.

Example 13

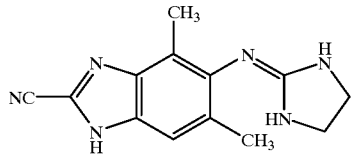

2-Cyano-4,6-dimethyl-5-(2-imidazolinylamino)benzimidazole

2-Amino-4,6-dimethyl-5-nitrobenzimidazole (as prepared in Example 11) is converted to 2-cyano-4,6-dimethyl-5-nitrobenzimidazole by treatment with sodium nitrite and tetrafluoroboric acid followed by reaction with copper cyanide. The synthesis of 2-cyano-4,6-dimethyl-5-(2-imidazolinylamino)benzimidazole is then completed according to Scheme 5.

Example 14

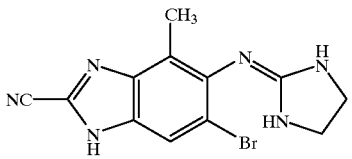

6-Bromo-2-cyano-5-(2-imidazolinylamino)-4-methylbenzimidazole 2-Amino-4-methyl-5-nitrobenzimidazole (see Example 12) is converted to 2-cyano-4-methyl-5-nitrobenzimidazole by first treating with sodium nitrate and tetrafluoroboric acid to form the diazonium salt, followed by reaction with copper cyanide. Reduction of the 5-nitro group followed by bromination (bromine, acetic acid) affords 5-amino-6-bromo-2-cyano-4-methylbenzimidazole. The synthesis is then completed according to Scheme 5.

Example 15

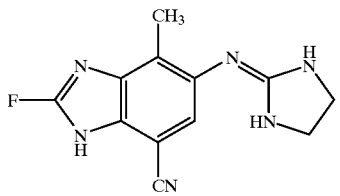

2-Fluoro-7-cyano-5-(2-imidazolinylamino)-4-methylbenzimidazole

3-Amino-2,6-dinitro-p-toluic carboxamide is converted to 7-carboxamido-2-diazo-4-methyl-5-nitrobenzimidazole tetrafluoroborate according to Scheme 4. Conversion to 7-carboxamido-2-fluoro-4-methyl-5-nitrobenzimidazole is achieved by thermal decomposition of the diazonium salt. The synthesis is then completed the same manner as in Example 1.

Example 16

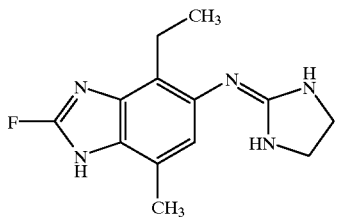

4-Ethyl-2-fluoro-5-(2-imidazolinylamino) benzimidazole 2,4-Dinitro-3-ethyl-6-methylaniline (see Example 2) is treated with sodium sulfide to afford 1,2-diamino-3-ethyl-6-methyl-4-nitrobenzene. Treatment with cyanogen bromide affords to 2-amino-4-ethyl-7-methyl-5-nitrobenzimidazole. This is converted to 2-diazo-4-ethyl-7-methyl-5-nitrobenzimidazole tetrafuoroborate with sodium nitrite and tetrafluoroboric acid. Thermal decomposition of the diazonium salt gives 4-ethyl-2-fluoro-7-methyl-5-nitrobenzimidazole. Conversion to 4-ethyl-2-fluoro-5-(2-imidazolinylamino)benzimidazole is completed according to Scheme 5.

Examples 17–39

Compounds of formula

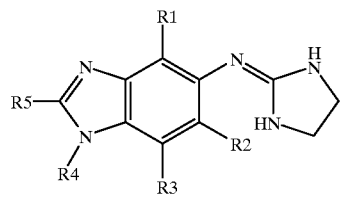

wherein R1, R2, R3, R4, and R5 are specified in the following table. Compounds of Example 17–39 are made using the methods explained and exemplified above.

| Example | R1 | R2 | R3 | R4 | R5 |
|---|---|---|---|---|---|
| 17 | methyl | H | cyano | H | bromo |
| 18 | methyl | H | cyano | H | chloro |
| 19 | methyl | H | cyano | H | hydroxy |
| 20 | methyl | H | hydroxy | H | H |
| 21 | methyl | H | hydroxy | methyl | H |
| 22 | methyl | H | hydroxy | H | methyl |
| 23 | methyl | H | hydroxy | H | fluoro |
| 24 | methyl | H | hydroxy | H | bromo |
| 25 | methyl | H | hydroxy | h | chloro |
| 26 | methyl | bromo | H | H | fluoro |
| 27 | methyl | bromo | H | H | bromo |
| 28 | methyl | bromo | H | H | hydroxy |
| 29 | methyl | bromo | H | methyl | H |
| 30 | methyl | chloro | H | H | H |
| 31 | methyl | chloro | H | methyl | H |
| 32 | methyl | chloro | H | H | amino |
| 33 | methyl | chloro | H | H | fluoro |
| 34 | methyl | chloro | H | H | bromo |
| 35 | methyl | chloro | H | H | methyl |
| 36 | methyl | methyl | H | methyl | H |
| 37 | methyl | methyl | H | H | hydroxy |
| 38 | methyl | methyl | H | H | fluoro |
| 39 | methyl | methyl | H | H | bromo |
| 40 | methyl | methyl | methyl | H | H |
| 41 | methyl | bromo | methyl | H | H |
| 42 | ethyl | H | bromo | H | H |
| 43 | ethyl | H | chloro | H | H |
| 44 | ethyl | H | hydroxy | H | H |
| 45 | ethyl | H | chloro | methyl | H |
| 46 | cyclopropyl | H | bromo | H | H |
| 47 | cyclopropyl | H | chloro | H | H |
| 48 | cyclopropyl | H | hydroxy | H | H |
| 49 | cyclopropyl | H | methyl | methyl | H |

Compositions

Another aspect of this invention is compositions which comprise a safe and effective amount of a compound of the invention, or a pharmaceutically-acceptable salt thereof, and a pharmaceutically-acceptable carrier. As used herein, "safe and effective amount" means an amount of the compound of the invention sufficient to significantly induce a positive modification in the condition to be treated, but low enough to avoid serious side effects (at a reasonable benefit/risk ratio), within the scope of sound medical judgment. A safe and effective amount of the compound of the invention will vary with the age and physical condition of the patient being treated, the severity of the condition, the duration of the treatment, the nature of concurrent therapy, the particular pharmaceutically-acceptable carrier utilized, and like factors within the knowledge and expertise of the attending physician.

Compositions of this invention preferably comprise from about 0.0001% to about 99% by weight of the compound of the invention, more preferably from about 0.01% to about 90%; also preferably from about 10% to about 50%, also preferably from about 5% to about 10%, also preferably from about 1% to about 5%, and also preferably from about 0.1% to about 1%.

In addition to the compound of the invention, the compositions of this invention contain a pharmaceutically-acceptable carrier. The term "pharmaceutically-acceptable carrier", as used herein, means one or more compatible solid or liquid filler diluents or encapsulating substances which are suitable for administration to a human or lower animal. The term "compatible", as used herein, means that the components of the composition are capable of being commingled with the compound of the invention, and with each other, in a manner such that there is no interaction which would substantially reduce the pharmaceutical efficacy of the composition under ordinary use situations. Pharmaceutically-acceptable carriers must, of course, be of sufficiently high purity and sufficiently low toxicity to render them suitable for administration to the human or lower animal being treated.

Some examples of substances which can serve as pharmaceutically-acceptable carriers or components thereof are sugars, such as lactose, glucose and sucrose; starches, such as corn starch and potato starch; cellulose and its derivatives, such as sodium carboxymethyl cellulose, ethyl cellulose, and methyl cellulose; powdered tragacanth; malt; gelatin; talc; solid lubricants, such as stearic acid and magnesium stearate; calcium sulfate; vegetable oils, such as peanut oil, cottonseed oil, sesame oil, olive oil, corn oil and oil of theobroma; polyols such as propylene glycol, glycerine, sorbitol, mannitol, and polyethylene glycol; alginic acid; emulsifiers, such as the Tweens®; wetting agents, such as sodium lauryl sulfate; coloring agents; flavoring agents; tableting agents; stabilizers; antioxidants; preservatives; pyrogen-free water; isotonic saline; and phosphate buffer solutions.

The choice of a pharmaceutically-acceptable carrier to be used in conjunction with the compound of the invention is basically determined by the way the compound is to be administered.

If the compound of the invention is to be injected, the preferred pharmaceutically-acceptable carrier is sterile, physiological saline, with blood-compatible suspending agent, the pH of which has been adjusted to about 7.4.

The preferred mode of administering the compound of the invention is perorally. The preferred unit dosage form is therefore tablets, capsules, lozenges, chewable tablets, and the like. Such unit dosage forms comprise a safe and effective amount of the compound of the invention, which is preferably from about 0.01 mg to about 200 mg, more preferably from about 0.1 mg to about 50 mg, more preferably still from about 0.5 mg to about 25 mg, also preferably from about 1 mg to about 10 mg. The pharmaceutically-acceptable carrier suitable for the preparation of unit dosage forms for peroral administration are well-known in the art. Tablets typically comprise conventional pharmaceutically-compatible adjuvants as inert diluents, such as calcium carbonate, sodium carbonate, mannitol, lactose and cellulose; binders such as starch, gelatin and sucrose; disintegrants such as starch, alginic acid and croscarmelose; lubricants such as magnesium stearate, stearic acid and talc. Glidants such as silicon dioxide can be used to improve flow characteristics of the powder mixture. Coloring agents, such as the FD&C dyes, can be added for appearance. Sweeteners and flavoring agents, such as aspartame, saccharin, menthol, peppermint, and fruit flavors, are useful adjuvants for chewable tablets. Capsules typically comprise one or more solid diluents disclosed above. The selection of carrier components depends on secondary considerations like taste, cost, and shelf stability, which are not critical for the purposes of this invention, and can be readily made by a person skilled in the art.

Peroral compositions also include liquid solutions, emulsions, suspensions, and the like. The pharmaceutically-acceptable carriers suitable for preparation of such compositions are well known in the art. Such liquid oral compositions preferably comprise from about 0.001% to about 5% of the compound of the invention, more preferably from about 0.01% to about 0.5%. Typical components of carriers for syrups, elixirs, emulsions and suspensions include ethanol, glycerol, propylene glycol, polyethylene glycol, liquid sucrose, sorbitol and water. For a suspension, typical suspending agents include methyl cellulose, sodium carboxymethyl cellulose, Avicel® R C-591, tragacanth and sodium alginate; typical wetting agents include lecithin and polysorbate 80; and typical preservatives include methyl paraben and sodium benzoate. Peroral liquid compositions may also contain one or more components such as sweeteners, flavoring agents and colorants disclosed above.

Other modes of administration useful for attaining systemic delivery of the compounds of the invention include subcutaneous, intravenous, sublingual and buccal dosage forms. Such compositions typically comprise one or more of soluble filler substances such as sucrose, sorbitol and mannitol; and binders such as acacia, microcrystalline cellulose, carboxymethyl cellulose and hydroxypropyl methyl cellulose. Glidants, lubricants, sweeteners, colorants, antioxidants and flavoring agents disclosed above may also be included.

A preferred mode of administering the compound of the invention is topically to the site where activity is desired: intranasal doses for nasal decongestion, inhalants for asthma, eye drops, gels and creams for ocular disorders.

Preferred intranasal compositions of this invention include aqueous solutions comprising a safe and effective amount of a compound of the invention. Such compositions preferably comprise from about 0.001% to about 5% of a compound of the invention, more preferably from about 0.01% to about 0.5%. Such compositions also typically include safe and effective amounts of preservatives, such as benzalkonium chloride and thimerosal; buffers such as phosphate and acetate; tonicity agents such as sodium chloride; antioxidants such as ascorbic acid; aromatic agents; and acids and bases to adjust the pH of these aqueous compositions as needed.

Preferred inhalation/atomization compositions of this invention include aqueous solutions, suspensions, and dry powders comprising a safe and effective amount of a compound of the invention. Such compositions preferably comprise from about 0.1% to about 50% of a compound of the invention, more preferably from about 1% to about 20%. Such compositions are typically contained in a container with attached atomizing means. Such compositions also typically include propellants such as chlorofluorocarbons 12/11 and 12/114; solvents such as water, glycerol and ethanol; stabilizers such as ascorbic acid, sodium metabisulfite; preservatives such as cetylpyridinium chloride and benzalkonium chloride; tonicity adjustors such as sodium chloride; and flavoring agents such as sodium saccharin.

Preferred intraocular compositions of this invention include aqueous solutions comprising a safe and effective amount of a compound of the invention. Such compositions preferably comprise from about 0.0001% to about 5% of a compound of the invention, more preferably from about 0.01% to about 0.5%. Such compositions also typically include one or more of preservatives, such as benzalkonium chloride, thimerosal, phenylmercuric acetate; vehicles, such as poloxamers, modified celluloses, povidone and purified water; tonicity adjustors, such as sodium chloride, mannitol and glycerin; buffers such as acetate, citrate, phosphate and borate; antioxidants such as sodium metabisulfite, butylated hydroxy toluene and acetyl cysteine; acids and bases may be used to adjust the pH of these formulations as needed.

Additional Drug Actives

Compositions of this invention may optionally include other drug actives. Non-limiting examples of drug actives which may be incorporated in these compositions include:

Antihistamines: Hydroxyzine preferably at a dosage range of from about 25 to about 400 mg; Doxylamine, preferably at a dosage range of from about 3 to about 75 mg; Pyrilamine, preferably at a dosage range of from about 6.25 to about 200 mg; Chlorpheniramine, preferably at a dosage range of from about 1 to about 24 mg; Phenindamine, preferably at a dosage range of from about 6.25 to about 150 mg; Dexchlorpheniramine, preferably at a dosage range of from about 0.5 to about 12 mg; Dexbrompheniramine, preferably at a dosage range of from about 0.5 to about 12 mg; Clemastine, preferably at a dosage range of from about 1 to about 9 mg; Diphenhydramine, preferably at a dosage range of from about 6.25 to about 300 mg; Azelastine, preferably at a dosage range of from about 140 to about 1,680 ug (when dosed intranasally); 1 to about 8 mg (when dosed orally); Acrivastine, preferably at a dosage range of from about 1 to about 24 mg; Levocarbastine (which can be dosed as an intranasal or ocular medicament), preferably at a dosage range of from about 100 to about 800 ug; Mequitazine, preferably at a dosage range of from about 5 to about 20 mg; Astemizole, preferably at a dosage range of from about 5 to about 20 mg; Ebastine;Loratadine, preferably at a dosage range of from about 5 to about 40 mg; Cetirizine, preferably at a dosage range of from about 5 to about 20 mg; Terfenadine, preferably at a dosage range of from about 30 to about 480 mg; Terfenadine metabolites; Promethazine, preferably at a dosage range of from about 6.25 to about 50 mg; Dimenhydrinate, preferably at a dosage range of from about 12.5 to about 400 mg; Meclizine, preferably at a dosage range of from about 6.25 to about 50 mg; Tripelennamine, preferably at a dosage range of from about 6.25 to about 300 mg; Carbinoxamine, preferably at a dosage range of from about 0.5 to about 16 mg; Cyproheptadine, preferably at a dosage range of from about 2 to about 20 mg; Azatadine, preferably at a dosage range of from about 0.25 to about 2 mg; Brompheniramine, preferably at a dosage range of from about 1 to about 24 mg; Triprolidine, preferably at a dosage range of from about 0.25 to about 10 mg; Cyclizine, preferably at a dosage range of from about 12.5 to about 200 mg; Thonzylamine, preferably at a dosage range of from about 12.5 to about 600 mg; Pheniramine, preferably at a dosage range of from about 3 to about 75 mg; Cyclizine, preferably at a dosage range of from about 12.5 to about 200 mg and others.

Antitussives: Codeine, preferably at a dosage range of from about 2.5 to about 120 mg; Hydrocodone, preferably at a dosage range of from about 2.5 to about 40 mg; Dextromethorphan, preferably at a dosage range of from about 2.5 to about 120 mg; Noscapine, preferably at a dosage range of from about 3 to about 180 mg; Benzonatate, preferably at a dosage range of from about 100 to about 600 mg; Diphenhydramine, preferably at a dosage range of from about 12.5 to about 150 mg; Chlophedianol, preferably at a dosage range of from about 12.5 to about 100 mg; Clobutinol, preferably at a dosage range of from about 20 to about 240 mg; Fominoben, preferably at a dosage range of from about 80 to about 480 mg; Glaucine; Pholcodine, preferably at a dosage range of from about 1 to about 40 mg; Zipeprol, preferably at a dosage range of from about 75 to about 300 mg; Hydromorphone, preferably at a dosage range of from about 0.5 to about 8 mg; Carbetapentane, preferably at a dosage range of from about 15 to about 240 mg; Caramiphen, Levopropoxyphene, preferably at a dosage range of from about 25 to about 200 mg and others.

Antiinflammatories, preferably Non-Steroidal Anti-inflammatories (NSAIDS): Ibuprofen, preferably at a dosage range of from about 50 to about 3,200 mg; Naproxen, preferably at a dosage range of from about 62.5 to about 1,500 mg; Sodium naproxen, preferably at a dosage range of from about 110 to about 1,650 mg; Ketoprofen, preferably at a dosage range of from about 25 to about 300 mg; Indoprofen, Indomethacin, preferably at a dosage range of from about 25 to about 200 mg; Sulindac, preferably at a dosage range of from about 75 to about 400 mg; Diflunisal, preferably at a dosage range of from about 125 to about 1,500 mg; Ketorolac, preferably at a dosage range of from about 10 to about 120 mg; Piroxicam, preferably at a dosage range of from about 10 to about 40 mg; Aspirin, preferably at a dosage range of from about 80 to about 4,000 mg; Meclofenamate, preferably at a dosage range of from about 25 to about 400 mg; Benzydamine, preferably at a dosage range of from about 25 to about 200 mg; Carprofen, preferably at a dosage range of from about 75 to about 300 mg; Diclofenac, preferably at a dosage range of from about 25 to about 200 mg; Etodolac, preferably at a dosage range of from about 200 to about 1,200 mg; Fenbufen, preferably at a dosage range of from about 300 to about 900 mg; Fenoprofen, preferably at a dosage range of from about 200 to about 3,200 mg; Flurbiprofen, preferably at a dosage range of from about 50 to about 300 mg; Mefenamic acid, preferably at a dosage range of from about 250 to about 1,500 mg; Nabumetone, preferably at a dosage range of from about 250 to about 2,000 mg; Phenylbutazone, preferably at a dosage range of from about 100 to about 400 mg; Pirprofen, preferably at a dosage range of from about 100 to about 800 mg; Tolmetin, preferably at a dosage range of from about 200 to about 1,800 mg and others.

Analgesics: Acetaminophen, preferably at a dosage range of from about 80 to about 4,000 mg; and others including narcotic and non-narcotic analgesics.

Expectorants/Mucolytics: Guaifenesin, preferably at a dosage range of from about 50 to about 2,400 mg; N-Acetylcysteine, preferably at a dosage range of from about 100 to about 600 mg; Ambroxol, preferably at a dosage range of from about 15 to about 120 mg; Bromhexine, preferably at a dosage range of from about 4 to about 64 mg; Terpin hydrate, preferably at a dosage range of from about 100 to about 1,200 mg; Potassium iodide, preferably at a dosage range of from about 50 to about 250 mg and others.

Atropinics, preferably intranasally or orally administered atropinics: Ipratroprium (preferably intranasally), preferably at a dosage range of from about 42 to about 252 ug; Atropine sulfate (preferably oral), preferably at a dosage range of from about 10 to about 1,000 ug; Belladonna (preferably as an extract), preferably at a dosage range of from about 15 to about 45 mg equivalents; Scopolamine, preferably at a dosage range of from about 400 to about 3,200 ug; Scopolamine methobromide, preferably at a dosage range of from about 2.5 to about 20 mg; Homatropine methobromide, preferably at a dosage range of from about 2.5 to about 40 mg; Hyoscyamine (preferably oral), preferably at a dosage range of from about 125 to about 1,000 ug; Isopropramide (preferably oral), preferably at a dosage range of from about 5 to about 20 mg; Orphenadrine (preferably oral), preferably at a dosage range of from about 50 to about 400 mg; Benzalkonium chloride (preferably intranasally) preferably a 0.005 to about 0.1% solution and others.

Mast Cell Stabilizers, preferably intranasally, or orally administered mast cell stabilizers: Cromalyn, preferably at a dosage range of from about 10 to about 60 mg; Nedocromil, preferably at a dosage range of from about 10 to about 60 mg; Oxatamide, preferably at a dosage range of from about 15 to about 120 mg; Ketotifen, preferably at a dosage range of from about 1 to about 4 mg; Lodoxamide, preferably at a dosage range of from about 100 to about 3,000 ug and others.

LT Antagonists: Zileuton and others.

Methylxanthines: Caffeine, preferably at a dosage range of from about about 65 to about 600 mg; Theophyllene, preferably at a dosage range of from about 25 to about 1,200 mg; Enprofylline; Pentoxifylline, preferably at a dosage range of from about 400 to about 3,600 mg; Aminophylline, preferably at a dosage range of from about 50 to about 800 mg; Dyphylline, preferably at a dosage range of from about 200 to about 1,600 mg and others.

Antioxidants or radical inhibitors: Ascorbic acid, preferably at a dosage range of from about 50 to about 10,000 mg; Tocopherol, preferably at a dosage range of from about 50 to about 2,000 mg; Ethanol, preferably at a dosage range of from about 500 to about 10,000 mg and others.

Steroids, preferably intranasally administered steroids: Beclomethasone, preferably at a dosage range of from about 84 to about 336 ug; Fluticasone, preferably at a dosage range of from about 50 to about 400 ug;

Budesonide, preferably at a dosage range of from about 64 to about 256 ug;

Mometasone; Triamcinolone, preferably at a dosage range of from about 110 to about 440 ug; Dexamethasone, preferably at a dosage range of from about 168 to about 1,008 ug; Flunisolide, preferably at a dosage range of from about 50 to about 300 ug; Prednisone (preferably oral), preferably at a dosage range of from about 5 to about 60 mg; Hydrocortisone (preferably oral), preferably at a dosage range of from about 20 to about 300 mg and others.

Bronchodilators, preferably for inhalation: Albuterol, preferably at a dosage range of from about 90 to about 1,080 ug; 2 to about 76 mg (if dosed orally); Epinephrine, preferably at a dosage range of from about 220 to about 1,320 ug; Ephedrine, preferably at a dosage range of from about 15 to about 240 mg (if dosed orally); 250 to about 1,000 ug (if dosed intranasally); Metaproterenol, preferably at a dosage range of from about 65 to about 780 ug or 10 to about 80 mg if dosed orally; Terbutaline, preferably at a dosage range of from about 200 to about 2,400 ug; 2.5 to about 20 mg if dosed orally; Isoetharine, preferably at a dosage range of from about 340 to about 1,360 ug; Pirbuterol, preferably at a dosage range of from about 200 to about 2,400 ug; Bitolterol, preferably at a dosage range of from about 370 to about 2,220 ug; Fenoterol, preferably at a dosage range of from about 100 to about 1,200 ug; 2.5 to about 20 mg (if dosed orally); Rimeterol, preferably at a dosage range of from about 200 to about 1,600 ug; Ipratroprium, preferably at a dosage range of from about 18 to about 216 ug (inhalation) and others.

Antivirals: Amantadine, preferably at a dosage range of from about 50 to about 200 mg; Rimantadine, preferably at a dosage range of from about 50 to about 200 mg; Enviroxime; Nonoxinols, preferably at a dosage range of from about 2 to about 20 mg (preferably an intranasal form); Acyclovir, preferably at a dosage range of from about 200 to about 2,000 mg (oral); 1 to about 10 mg (preferably an intranasal form); Alpha-interferon, preferably at a dosage range of from about 3 to about 36 MIU; Beta-Interferon, preferably at a dosage range of from about 3 to about 36 MIU and others.

Ocular Drug actives: acetylcholinesterase inhibitors, e.g., echothiophate from about 0.03% to about 0.25% in topical solution and others; and Gastrointestinal actives: antidiarrheals, e.g., loperamide from about 0.1 mg to about 1.0 mg per dose, and bismuth subsalicylate from about 25 mg to about 300 mg per dose and others.

An active may be useful for more than one of the above uses, and these uses are clearly contemplated as well. This overlap is recognized in the art and adjusting dosages and the like to fit the indication is well within the ability of the skilled medical practitioner.

Methods of use

The compounds of the present invention are useful in treating many medical disorders, including for example, respiratory disorders, ocular disorders, gastrointestinal disorders, disorders associated with sympathetic nervous system activity, migraine, peripheral pain, and disorders where vasoconstriction would provide a benefit.

The preferred routes of administration are peroral; intranasal; parenteral; subcutaneous; and topical.

Another aspect of the invention involves methods for preventing or treating nasal congestion by administering a safe and effective amount of a subject compound to a human or lower animal experiencing or at risk of experiencing nasal congestion. Such nasal congestion may be associated with human diseases or disorders which include, but are not limited to, seasonal allergic rhinitis, acute upper respiratory viral infections, sinusitis, perennial rhinitis, and vasomotor rhinitis. Each administration of a dose of the subject compound preferably administers a dose within the range of from about 0.001 mg/kg to about 10 mg/kg of a compound, more preferably from about 0.01 mg/kg to about 5 mg/kg, more preferably still from about 0.1 mg/kg to about 1 mg/kg. Peroral or intranasal administration of such doses is preferred. The frequency of administration of a subject compound according to this invention is preferably from about once to about six times daily, more preferably from about 2 times to about 4 times daily. Such doses and frequencies are also preferred for treating other respiratory conditions, such as otitis media, cough, COPD and asthma.

Another aspect of this invention involves methods for preventing or treating glaucoma by administering a safe and effective amount of a subject compound to a mammal experiencing or at risk of experiencing glaucoma. If administered systemically, each administration of a dose of the subject compound preferably administers a dose within the range of from about 0.0001 mg/kg to about 5 mg/kg of a compound, more preferably from about 0.001 mg/kg to about 0.5 mg/kg. If intraocular dosing is used then preferably one administers a typical volume (for example, 1 or 2 drops) of a liquid composition, comprising from about 0.0001% to about 5% of a subject compound, more preferably from about 0.01% to about 0.5% of the compound. Determination of the exact dosage and regimen is within the purview of the skilled artisan. Intraocular administration of such doses is preferred. The frequency of administration of a subject compound according to this invention is preferably from about once to about six times daily, more preferably from about once to about 4 times daily.

Another aspect of this invention involves methods for preventing or treating migraine, by administering a safe and effective amount of a subject compound to a human or lower animal experiencing or at risk of experiencing migraine. Each administration of a dose of the subject compound preferably administers a dose within the range of from about 0.001 mg/kg to about 10 mg/kg of a compound, more preferably from about 0.01 mg/kg to about 5 mg/kg, more preferably still from about 0.1 mg/kg to about 1 mg/kg. Peroral or intranasal administration of such doses is preferred. The frequency of administration of a subject compound according to this invention is preferably from about once to about six times daily, more preferably from about 2 times to about 4 times daily.

Another aspect of this invention involves methods for preventing or treating functional bowel disorders, such as diarrhea, by administering a safe and effective amount of a subject compound to a human or lower animal experiencing or at risk of experiencing diarrhea. Each administration of a dose of the subject compound preferably administers a dose within the range of from about 0.001 mg/kg to about 10 mg/kg of a compound, more preferably from about 0.01 mg/kg to about 5 mg/kg, more preferably still from about 0.1 mg/kg to about 1 mg/kg. Peroral administration of such doses is preferred. The frequency of administration of a subject compound according to this invention is preferably from about once to about six times daily, more preferably from about 2 times to about 4 times daily.

Dosages may be varied based on the patient being treated, the condition being treated, the severity of the condition being treated, the route of administration, etc. to achieve the desired effect.

Composition and Method Examples

The following non-limiting examples illustrate the subject invention. The following composition and method examples do not limit the invention, but provide guidance to the skilled artisan to prepare and use the compounds, compositions and methods of the invention. In each case other compounds within the invention may be substituted for the example compound shown below with similar results. The skilled practitioner will appreciate that the examples provide guidance and may be varied based on the condition being treated and the patient.

Example A

Oral Tablet Composition

| Ingredient | Amount per tablet (mg) |
|---|---|
| Compound of Example 1 | 20.0 |
| Microcrystaliine cellulose (Avicel PH 102 ®) | 80.0 |
| Dicalcium phosphate | 96.0 |
| Pyrogenic silica (Cab-O-Sil ®) | 1.0 |
| Magnesium stearate | 3.0 |
| Total = | 200.0 |

One tablet is swallowed by a patient with nasal congestion. The congestion is substantially diminished.

Example B

Chewable Tablet Composition

| Ingredient | Amount per tablet (mg) |
|---|---|
| Compound of Example 2 | 15.0 |
| Mannitol | 255.6 |
| Microcrystaliine cellulose (Avicel PH 101 ®) | 100.8 |
| Dextrinized sucrose (Di-Pac ®) | 199.5 |
| Imitation orange flavor | 4.2 |
| Sodium saccharin | 1.2 |
| Stearic acid | 15.0 |
| Magnesium stearate | 3.0 |
| FD&C Yellow #6 dye | 3.0 |
| Pyrogenic silica (Cab-O-Sil ®) | 2.7 |
| Total = | 600.0 |

One tablet is chewed and swallowed by a patient with nasal congestion. The congestion is substantially reduced.

Example C

Sublingual Tablet Composition

| Ingredient | Amount per tablet (mg) |
|---|---|
| Compound of Example 3 | 2.00 |
| Mannitol | 2.00 |
| Microcrystalline cellulose (Avicel PH 101 ®) | 29.00 |
| Mint flavorants | 0.25 |
| Sodium saccharin | 0.08 |
| Total = | 33.33 |

One tablet is placed under the tongue of a patient with nasal congestion and allowed to dissolve. The congestion is rapidly and substantially diminished.

Example D

Intranasal Solution Composition

| Ingredient | Composition (% w/v) |
|---|---|
| Compound of Example 4 | 0.20 |
| Benzalkonium chloride | 0.02 |
| Thimerosal | 0.002 |
| d-Sorbitol | 5.00 |
| Glycine | 0.35 |
| Aromatics | 0.075 |
| Purified water | q.s. |
| Total = | 100.00 |

One-tenth of a mL of the composition is sprayed from a pump actuator into each nostril of a patient with nasal congestion. The congestion is substantially diminished.

Example E

Intranasal Gel Composition

| Ingredient | Composition (% w/v) |
|---|---|
| Compound of Example 5 | 0.10 |
| Benzalkonium chloride | 0.02 |
| Thimerosal | 0.002 |
| Hydroxypropyl methylcellulose (Metolose 65SH4000 ®) | 1.00 |
| Aromatics | 0.06 |
| Sodium chloride (0.65%) | q.s. |
| Total = | 100.00 |

One-fifth of a mL of the composition is applied as drops from a dropper into each nostril of a patient with nasal congestion. The congestion is substantially reduced.

Example F

Inhalation Aerosol Composition

| Ingredient | Composition (% w/v) |
|---|---|
| Compound of Example 1 | 5.0 |
| Alcohol | 33.0 |
| Ascorbic acid | 0.1 |
| Menthol | 0.1 |
| Sodium Saccharin | 0.2 |
| Propellant (F12, F114) | q.s. |
| Total = | 100.0 |

Two-puffs of the aerosol composition is inhaled from a metered-dose inhaler by a patient with asthma. The asthmatic condition is effectively relieved.

Example G

Topical Ophthalmic Composition

| Ingredient | Composition (% w/v) |
|---|---|
| Compound of Example 7 | 0.10 |
| Benzalkonium chloride | 0.01 |
| EDTA | 0.05 |
| Hydroxyethylcellulose (Natrosol M ®) | 0.50 |
| Sodium metabisulfite | 0.10 |
| Sodium chloride (0.9%) | q.s. |
| Total = | 100.0 |

One-tenth of a mL of the composition is administered directly into each eye of a patient with glaucoma. The intraocular pressure is substantially reduced.

Example H

Oral Liquid Composition

| Ingredient | Amount/15 mL Dose |
| --- | --- |
| Compound of Example 1 | 15 mg |
| Chlorpheniramine maleate | 4 mg |
| Propylene glycol | 1.8 g |
| Ethanol (95%) | 1.5 mL |
| Methanol | 12.5 mg |
| Eucalyptus oil | 7.55 mg |
| Flavorants | 0.05 mL |
| Sucrose | 7.65 g |
| Carboxymethylcellulose (CMC) | 7.5 mg |
| Microcrystalline cellulose and Sodium CMC (Avicel RC 591 ®) | 187.5 mg |
| Polysorbate 80 | 3.0 mg |
| Glycerin | 300 mg |
| Sorbitol | 300 mg |
| FD&C Red #40 dye | 3 mg |
| Sodium saccharin | 22.5 mg |
| Sodium phosphate monobasic | 44 mg |
| Sodium citrate monohydrate | 28 mg |
| Purified Water | q.s. |
| Total = | 15 mL |

One 15 mL dose of the liquid composition is swallowed by a patient with nasal congestion, runny nose and sneezing due to allergic rhinitis. The congestion, runny nose and sneezing are effectively reduced.

Example J

Oral Liquid Composition

| Ingredient | Amount/15 mL Dose |
| --- | --- |
| Compound of Example 7 | 30 mg |
| Sucrose | 8.16 g |
| Glycerin | 300 mg |
| Sorbitol | 300 mg |
| Methylparaben | 19.5 mg |
| Propylparaben | 4.5 mg |
| Menthol | 22.5 mg |
| Eucalyptus oil | 7.5 mg |
| Flavorants | 0.07 mL |
| FD&C Red #40 dye | 3.0 mg |
| Sodium saccharin | 30 mg |
| Purified water | q.s. |
| Total = | 15 mL |

One 15 mL dose of the alcohol-free liquid medication is swallowed by a patient with nasal congestion. The congestion is substantially diminished.

Example K

Oral Tablet composition

| Ingredient | Amount per tablet (mg) |
| --- | --- |
| Chlorpheniramine maleate, USP | 4.0 |
| Compound of Example 8 | 4.0 |
| Microcrystalline cellulose, NF | 130.0 |
| Starch 1500, NF | 100.0 |
| Magnesium stearate, USP | 2.0 |
| Total = | 240.0 |

For the relief of nasal congestion due to the common cold, hay fever, or other upper respiratory allergies, or associated with sinusitis; relieves runny nose, sneezing, and itchy watery eyes as may occur in allergic rhinitis. Restores freer breathing through the nose. Adults 12 and over take one tablet every four hours.

Example L

Oral Tablet Composition

| Ingredient | Amount per tablet (mg) |
| --- | --- |
| Loratadine | 5.0 |
| Compound of Example 9 | 12.0 |
| Hydroxypropyl methylcellulose, USP | 12.0 |
| Magnesium stearate, USP | 2.0 |
| Lactose anhydrous, USP | 200.0 |
| Total = | 231.0 |

For the relief of symptoms associated with allergic rhinitis such as sneezing, rhinorrhea, and nasal congestion. Adults 12 and over take one tablet every twelve hours.

Example M

Oral Caplet Composition

| Ingredient | Amount per caplet (mg) |
| --- | --- |
| Naproxen sodium anhydrous, USP | 220.0 |
| Compound of Example 10 | 6.0 |
| Hydroxypropyl methylcellulose, USP | 6.0 |
| Magnesium stearate, USP | 2.0 |
| Povidone K-30, USP | 10.0 |
| Talc, USP | 12.0 |
| Microcrystalline cellulose, NF | 44.0 |
| Total = | 300.0 |

For relief of symptoms associated with the common cold, sinusitis, or flu including nasal congestion, headache, fever, body aches, and pains. Adults 12 and over take two caplets every twelve hours.

Example N

Oral Tablet Composition

| Ingredient | mg/tablet |
| --- | --- |
| Acetaminophen, USP | 500.0 |
| Compound of Example 1 | 6.0 |
| Hydroxypropyl methylcellulose, USP | 6.0 |
| Silicon dioxide, colloidal, NF | 30.0 |
| Pregelatinized starch, NF | 50.0 |
| Magnesium stearate, USP | 4.0 |
| Total = | 596.0 |

For relief of nasal/sinus congestion and pressure, sinus headache pain associated with sinusitis, hay fever, upper respiratory allergies, or the common cold. Adults 12 and over take one tablet every six hours.

Example O

| Oral Caplet Composition | |
|---|---|
| Ingredient | Amount per caplet (mg) |
| Naproxen sodium anhydrous, USP | 220.0 |
| Loratadine | 2.5 |
| Compound of Example 3 | 6.0 |
| Hydroxypropyl methylcellulose, USP | 6.0 |
| Magnesium stearate, USP | 2.0 |
| Povidone K-30, USP | 10.5 |
| Talc, USP | 12.0 |
| Microcystalline cellulose, NF | 44.0 |
| Total = | 303.0 |

For the relief of symptoms associated with allergic rhinitis such as sneezing, rhinorrhea, nasal congestion, sinus pain, and headache. Adults 12 and over take two caplets every twelve hours.

Example P

| Oral Tablet Composition | |
|---|---|
| Ingredient | Amount per tablet (mg) |
| Naproxen sodium anhydrous, USP | 220.0 |
| Chlorpheniramine maleate, USP | 6.0 |
| Compound of Example 2 | 6.0 |
| Hydroxypropyl methylcellulose, USP | 12.0 |
| Magnesium stearate, USP | 2.0 |
| Povidone K-30, USP | 10.0 |
| Talc, USP | 12.0 |
| Microcrystalline cellulose, NF | 44.0 |
| Total = | 312.0 |

For the relief of symptoms due to the common cold, flu, hay fever, or other upper respiratory allergies, or associated with sinusitis; relieves runny nose, sneezing, and itchy watery eyes as may occur in allergic rhinitis. Relieves headache, fever, body aches, and pains. Restores freer breathing through the nose. Adults 12 and over take two tablets every twelve hours.

Example Q

| Oral Tablet Composition | |
|---|---|
| Ingredient | Amount per tablet (mg) |
| Acetaminophen, USP | 500.0 |
| Loratadine | 1.3 |
| Compound of Example 4 | 3.0 |
| Hydroxypropyl methylcellulose, USP | 3.0 |
| Silicon dioxide, colloidal, NF | 30.0 |
| Pregelatinized starch, NF | 50.0 |
| Magnesium stearate, USP | 2.7 |
| Total = | 590.0 |

For the relief of symptoms associated with allergic rhinitis such as sneezing, rhinorrhea, nasal congestion, sinus pain, and headache. Adults 12 and over take two tablets every six hours.

Example R

| Oral Tablet Composition | |
|---|---|
| Ingredient | Amount per tablet (mg) |
| Compound of Example 1 | 20.0 |
| Microcrystalline cellulose (Avicel PH 102 ®) | 80.0 |
| Dicalcium phosphate | 96.0 |
| Pyrogenic silica (Cab-O-Sil ®) | 1.0 |
| Magnesium stearate | 3.0 |
| Total = | 200.0 |

One tablet is swallowed by a patient with migraine. The pain and aura of migraine is substantially diminished.

Example S

| Oral Tablet Composition | |
|---|---|
| Ingredient | Amount per tablet (mg) |
| Compound of Example 1 | 20.0 |
| Microcrystalline cellulose (Avicel PH 102 ®) | 80.0 |
| Dicalcium phosphate | 96.0 |
| Pyrogenic silica (Cab-O-Sil ®) | 1.0 |
| Magnesium stearate | 3.0 |
| Total = | 200.0 |

One tablet is swallowed by a patient with diarrhea. The diarrhea is substantially diminished.

Other examples of combination actives are contemplated. Examples of medicaments which can be combined with the primary active are included in U.S. Pat. No. 4,552,899 to Sunshine, et al., hereby incorporated by reference. All other references referred to throughout this specification are hereby incorporated by reference.

While particular embodiments of this invention have been described, it will be obvious to those skilled in the art that various changes and modifications of this invention can be made without departing from the spirit and scope of the invention. It is intended to cover, in the appended claims, all such modifications that are within the scope of this invention.

What is claimed is:

1. A compound having the following structure:

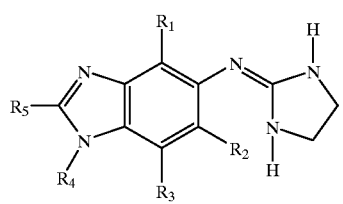

wherein:
(a) R1 is alkyl;
(b) R2 is selected from the group consisting of: hydrogen, alkyl, methoxy, cyano, and halo;
(c) R3 is selected form the group consisting of: hydrogen, methyl, hydroxy, cyano and halo;
(d) R4 is hydrogen;

(e) R5 is selected from the group consisting of: hydrogen, methyl, amino, methoxy, hydroxy, cyano and halo;

(f) provided that at least one of R2, R3, or R5 is other than hydrogen or fluorine;

(g) provided that when R1 is methyl and both R2 and R5 are hydrogen, R3 is other than methyl or halo;

(h) provided that when R3 is cyano, R1 is methyl; and any tautomer of the above structure or pharmaceutically acceptable salt, or biohydrolyzable ester, amide, or imide thereof.

2. The compound according to claim 1 characterized in that R2 and R5 are independently selected from the group consisting of: hydrogen, methyl, and halo.

3. The compound according to claim 1 or 2 characterized in that R1 is methyl and R3 is cyano or hydroxy.

4. The compound according to claim 1 or 2 characterized in that R1 is ethyl or cyclopropyl and R3 is selected from the group consisting of: methyl, hydroxy, and halo.

5. The compound according to claim 1 characterized in that the compound is selected from the group consisting of: 7-cyano-5-(2-imidazolinylamino)-4-methylbenzimidazole, 7-hydroxy-5-(2-imidazolinylamino)-4-methylbenzimidazole, 4-ethyl-5-(2-imidazolinylamino)-7-methylbenzimidazole, and 4-cyclopropyl-5-(2-imidazolinylamino)-7-methylbenzimidazole.

6. A pharmaceutical composition comprising:

(a) a safe and effective amount of a compound of claim 1, and (b) a pharmaceutically-acceptable carrier.

7. A method of preventing or treating alpha-2 mediated disorders by administering to a human or lower animal in need of such treatment, a safe and effective amount of a compound of claim 1.

8. The method of claim 7 wherein the disorder is selected form the group consisting of: respiratory disorder, ocular disorder, gastrointestinal disorder, a disorder associated with sympathetic nervous system activity, migraine, peripheral pain, and a disorder where vasoconstriction would provide a benefit.

9. The method of claim 8 wherein the disorder is nasal congestion.

10. The method of claim 8 wherein the disorder is glaucoma.

11. The method of claim 8 wherein the disorder is asthma.

12. The method of claim 8 wherein the disorder is migraine.

13. The method of claim 8 wherein the disorder is diarrhea.

14. A pharmaceutical composition comprising the compound of claim 1 and one or more actives chosen from the group consisting of an antihistamine, antitussive, mast cell stabilizer, LT antagonist, expectorant/mucolytic, antioxidant or radical inhibitor, steroid, bronchodilator, antiviral, analgesic, anti-inflammatory, gastrointestinal, and ocular active.

15. The pharmaceutical composition of claim 6 wherein R1 is methyl, R2 is hydrogen, R3 is cyano, R4 is hydrogen, and R5 is hydrogen.

16. The pharmaceutical composition of claim 14 wherein R1 is methyl, R2 is hydrogen, R3 is cyano, R4 is hydrogen, and R5 is hydrogen.

17. The method of claim 7 wherein R1 is methyl, R2 is hydrogen, R3 is cyano, R4 is hydrogen, and R5 is hydrogen.

18. The method of claim 8 wherein R1 is methyl, R2 is hydrogen, R3 is cyano, R4 is hydrogen, and R5 is hydrogen.

19. The method of claim 8 wherein the disorder is peripheral pain.

* * * * *